US008649869B2

(12) United States Patent
Imani et al.

(10) Patent No.: US 8,649,869 B2
(45) Date of Patent: Feb. 11, 2014

(54) IMPLANTABLE MEDICAL DEVICE HAVING FEEDTHRU ASSEMBLY WITH HEADER SIDE BUNCHED CONDUCTOR ARRAY AND CAN SIDE LINEAR CONDUCTOR ARRAY

(75) Inventors: Reza Imani, Moorpark, CA (US); Micah Meulmester, Santa Monica, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/412,485

(22) Filed: Mar. 5, 2012

(65) Prior Publication Data

US 2013/0231718 A1 Sep. 5, 2013

(51) Int. Cl.
*A61N 1/00* (2006.01)

(52) U.S. Cl.
USPC .......................................................... 607/37

(58) Field of Classification Search
USPC ...................................................... 607/36–38
See application file for complete search history.

(56) References Cited

U.S. PATENT DOCUMENTS

| 5,750,926 | A | | 5/1998 | Schulman et al. | |
|---|---|---|---|---|---|
| 5,866,851 | A | * | 2/1999 | Taylor et al. | 174/152 GM |
| 7,068,491 | B1 | * | 6/2006 | Burdon et al. | 361/313 |
| 7,310,216 | B2 | * | 12/2007 | Stevenson et al. | 361/302 |
| 2007/0053137 | A1 | | 3/2007 | Fu et al. | |
| 2011/0066212 | A1 | | 3/2011 | Stevenson et al. | |
| 2011/0102967 | A1 | | 5/2011 | Munns et al. | |

FOREIGN PATENT DOCUMENTS

| EP | 1760735 A1 | 3/2007 |
|---|---|---|
| EP | 1834666 A2 | 9/2007 |
| WO | 2007035332 A1 | 3/2007 |

\* cited by examiner

*Primary Examiner* — Scott Getzow

(57) ABSTRACT

An implantable pulse generator includes a header, a can, a grouped array feedthru, and an inline array feedthru board. The feedthru includes a header side, a can side and a grouped array of feedthru wires extending through the feedthru. A first end of each feedthru wire is electrically coupled to a lead connector block. The inline array feedthru board includes a grouped array of first electrical contact holes and an inline array of conductor wires. The grouped array of first electrical contact holes receives therein second ends of the feedthru wires. The inline array of conductor wires projects from a side of the board opposite the feedthru. Each first electrical contact hole is in electrical communication with a respective conductor wire. Each conductor wire is in electrical contact with at least a portion of an electrical connection region of an electronic substrate housed within the can.

30 Claims, 22 Drawing Sheets

IMPLANTABLE MEDICAL DEVICE HAVING FEEDTHRU ASSEMBLY WITH HEADER SIDE BUNCHED CONDUCTOR ARRAY AND CAN SIDE LINEAR CONDUCTOR ARRAY

CROSS REFERENCE TO RELATED APPLICATIONS

This application is related to copending U.S. patent application Ser. No. 12/607,893, filed Oct. 28, 2009, titled "Implantable Medical Device Having Feedthru with an Integrated Interconnect/Filter Substrate."

FIELD OF THE INVENTION

The present invention relates to medical apparatus and methods. More specifically, the present invention relates to feedthrus for implantable pulse generators and methods of manufacturing such feedthrus.

BACKGROUND OF THE INVENTION

Implantable pulse generators, including cardiovascular implantable electronic devices ("CIED") such as pacemakers and implantable cardioverter defibrillators ("ICD"), are used to provide therapy to cardiac tissue, nerves and other tissue via implantable leads. An implantable pulse generator feedthru is used for an electrical pathway extending between the electrically conductive lead securing components of a header of the pulse generator and the electrical components, such as an output flex, hybrid, etc., hermetically sealed in the housing or can of the pulse generator.

Feedthrus provide insulated passageways for feedthru wires, such as platinum iridium (Pt/Ir) wires, through the wall of the can. The header ends of the feedthru wires are electrically connected to connector blocks that mechanically and electrically couple with proximal connector ends of implantable leads, and the can ends of the feedthru wires are electrically connected to the electrical components housed in the can of the pulse generator.

For purposes of patient comfort and the ability to implant pulse generators in a variety of locations to allow the pulse generator to be used for a variety of patient treatments, there is a constant need to reduce the size of pulse generators to the greatest extent possible. Unfortunately, the need to reduce the size of pulse generators typically has the undesirable result of increased manufacturing costs and/or adverse impacts on pulse generator robustness and reliability.

There is a need in the art for an implantable pulse generator having reduced size, reduced manufacturing costs and improved robustness and reliability. There is also a need in the art for methods of manufacturing such an implantable pulse generator.

BRIEF SUMMARY OF THE INVENTION

Disclosed herein is an implantable pulse generator. In a first embodiment, the implantable pulse generator includes a header, a can, a grouped array feedthru, and an inline array feedthru board. The header includes lead connector blocks. The can is coupled to the header and includes a wall and an electronic substrate housed within the wall. The electronic substrate includes an electrical connection region. The feedthru is mounted in the wall and includes a header side, a can side and a grouped array of feedthru wires extending through the feedthru. Each feedthru wire has a first end and a second end opposite the first end. The first end is electrically coupled to a lead connector block of the lead connector blocks. The inline array feedthru board is adjacent the can side and includes a grouped array of first electrical contact holes and an inline array of conductor wires. The grouped array of first electrical contact holes receives therein the second ends. The inline array of conductor wires projects from a side of the board opposite the feedthru. Each first electrical contact hole is in electrical communication with a respective conductor wire. Each conductor wire is in electrical contact with at least a portion of the electrical connection region.

In one version of the first embodiment of the pulse generator, the grouped array of feedthru wires is two rows of four feedthru wires and the inline array of conductor wires is a single line of at least eight conductor wires. Alternatively, the grouped array of feedthru wires is two rows of three feedthru wires and the inline array of conductor wires is a single line of at least six conductor wires, or the grouped array of feedthru wires is two rows of two feedthru wires and the inline array of conductor wires is a single line of at least four conductor wires.

In one version of the first embodiment of the pulse generator, the pulse generator also includes an EMI filter coupled to the feedthru. For example, the EMI filter is sandwiched between the feedthru and board, and the grouped array of feedthru wires extend through the EMI filter before being received in the grouped array of first electrical contact holes. While the EMI filter may be in the form of a multi-layered configuration attached to the can side of the feedthru, in other embodiments, the EMI filter may instead be at least one of a discoidal capacitor or a discrete capacitor.

In one version of the first embodiment of the pulse generator, the board includes respective conductive traces extending through a body of the board so each first electrical contact hole is in electrical communication with a respective conductor wire. Also, the pulse generator may further include a ground wire extending from the board on a side opposite a side from which the conductor wires extend. Such a ground wire may be in electrical contact with a conductor wire of the inline array and a housing of the feedthru.

In one version of the first embodiment of the pulse generator, the electrical connection region may include a plug-in type electrical connector having an inline array of second electrical contact holes and each conductor wire is received in a respective second electrical contact hole. In another version of the first embodiment, the electrical connection region may include at least one of wire bonding pads or Kovar tabs and each conductor wire is electrically coupled to a respective pad or tab. In yet another version of the first embodiment, the electrical connection region may include a portion of the electronic substrate configured for at least one of wire bonding, welding or soldering each conductor wire to the portion of the electronic substrate.

In a second embodiment, the implantable pulse generator includes a header, a can, and a feedthru assembly. The header includes lead connector blocks. The can is coupled to the header and includes a wall and an electronic substrate housed within the wall. The electronic substrate includes an electrical connection region. The feedthru assembly includes a feedthru mounted in the wall and a feedthru board coupled to the feedthru and housed within the wall. A grouped array of feedthru wires extends from the connector blocks, through the feedthru and into the feedthru board. A linear array of conductor wires extends from a side of the board opposite the feedthru. Each feedthru wire is in electrical communication with a respective conductor wire. Each conductor wire is received in the electrical connection region.

In one version of the second embodiment of the pulse generator, the grouped array of feedthru wires is two rows of four feedthru wires and the linear array of conductor wires is a single line of at least eight conductor wires. Alternatively, the grouped array of feedthru wires is two rows of three feedthru wires and the linear array of conductor wires is a single line of at least six conductor wires, or the grouped array of feedthru wires is two rows of two feedthru wires and the linear array of conductor wires is a single line of at least four conductor wires.

In one version of the second embodiment of the pulse generator, the pulse generator also includes an EMI filter coupled to the feedthru. For example, the EMI filter is sandwiched between the feedthru and board, and the grouped array of feedthru wires extend through the EMI filter before being received in the grouped array of second electrical contact holes. While the EMI filter may be in the form of a multi-layered configuration attached to the can side of the feedthru, in other embodiments, the EMI filter may instead be at least one of a discoidal capacitor or a discrete capacitor.

In one version of the second embodiment of the pulse generator, the board includes respective conductive traces extending through a body of the board so each feedthru wire is in electrical communication with a respective conductor wire. Also, the pulse generator may also include a ground wire extending from the board on a side opposite a side from which the conductor wires extend. Such a ground wire may be in electrical contact with a conductor wire of the linear array and a housing of the feedthru.

In one version of the second embodiment of the pulse generator, the electrical connection region may include a plug-in type electrical connector having an inline array of electrical contact holes and each conductor wire is received in a respective electrical contact hole. In another version of the first embodiment, the electrical connection region may include at least one of wire bonding pads or Kovar tabs and each conductor wire is electrically coupled to a respective pad or tab. In yet another version of the first embodiment, the electrical connection region may include a portion of the electronic substrate configured for at least one of wire bonding, welding or soldering each conductor wire to the portion of the electronic substrate.

Also disclosed herein is a method of manufacturing an implantable pulse generator. In one embodiment, the method includes: providing a feedthru assembly having a bunched array of feedthru wires extending from a header side of a feedthru of the assembly and a linear array of conductor wires extending from a can side of a feedthru board of the assembly, the feedthru board being adjacent a can side of the feedthru; coupling the bunched array of feedthru wires to connector blocks in a header of the pulse generator; and extending the linear array of conductor wires into an electrical connection region of an electronic substrate housed within a can of the pulse generator.

For the embodiment of the method, the feedthru assembly may be configured to transition the bunched array of feedthru wires into the linear array of conductor wires. Also, the feedthru assembly may include an EMI filter sandwiched between he feedthru and feedthru board, and the bunched array of feedthru wires may extend through the EMI filter and into the feedthru board. The bunched array of feedthru wires may include multiple rows of multiple feedthru wires, and the linear array of conductor wires may include a singe line of multiple conductor wires.

For the embodiment of the method, extending the linear array of conductor wires into an electrical connection region includes plugging the linear array of conductor wires into a linear array of contact holes of a plug-in type connector electrically coupled to the electronic substrate housed within the can of the pulse generator. Alternatively, extending the linear array of conductor wires into an electrical connection region includes electrically coupling the linear array of conductor wires to at least one of wire bond pads or Kovar tabs electrically coupled to the electronic substrate housed within the can of the pulse generator.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1A:
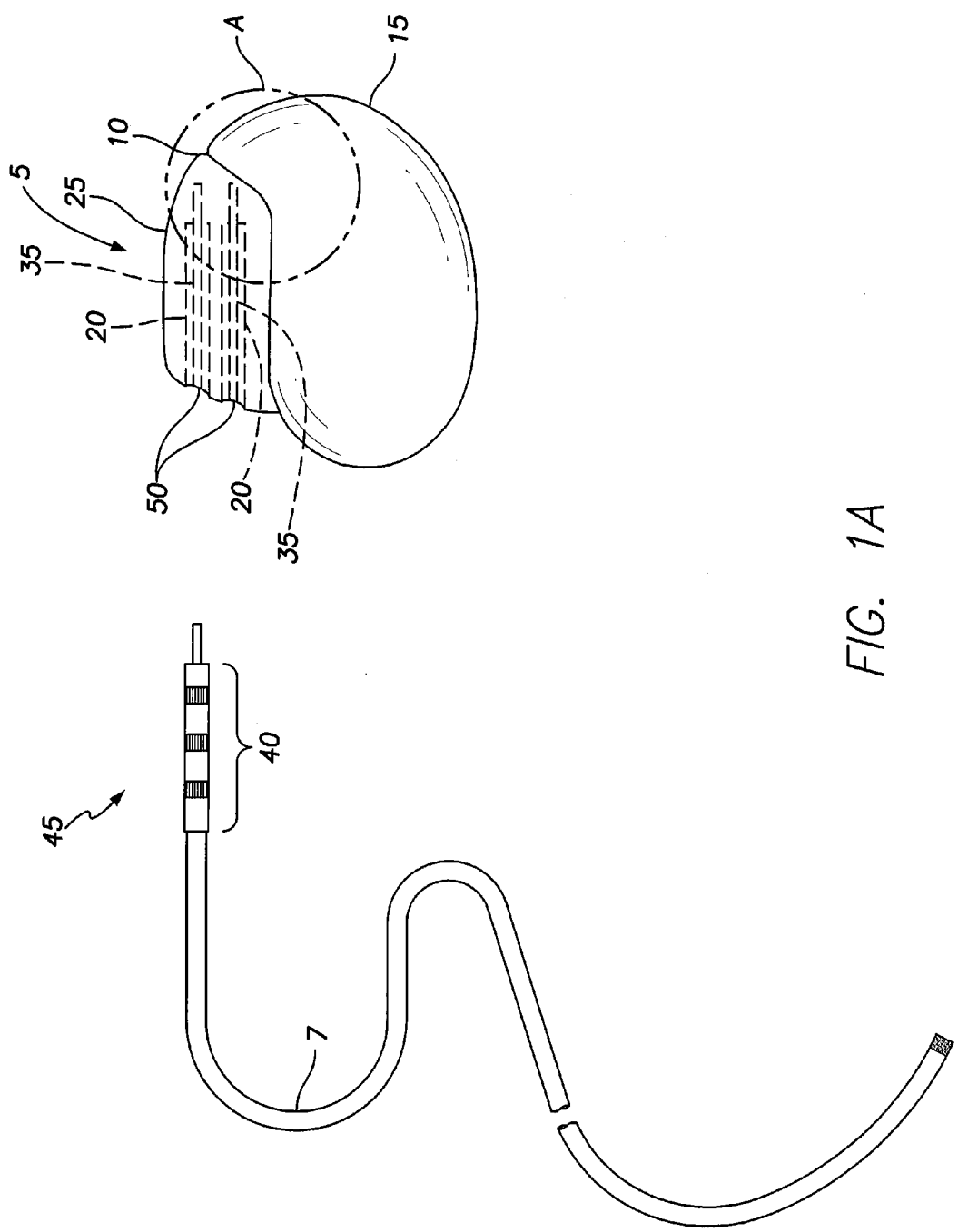
FIG. 1A is a side view of a pulse generator and an implantable lead positioned to be coupled to the pulse generator.
Figure 1B:
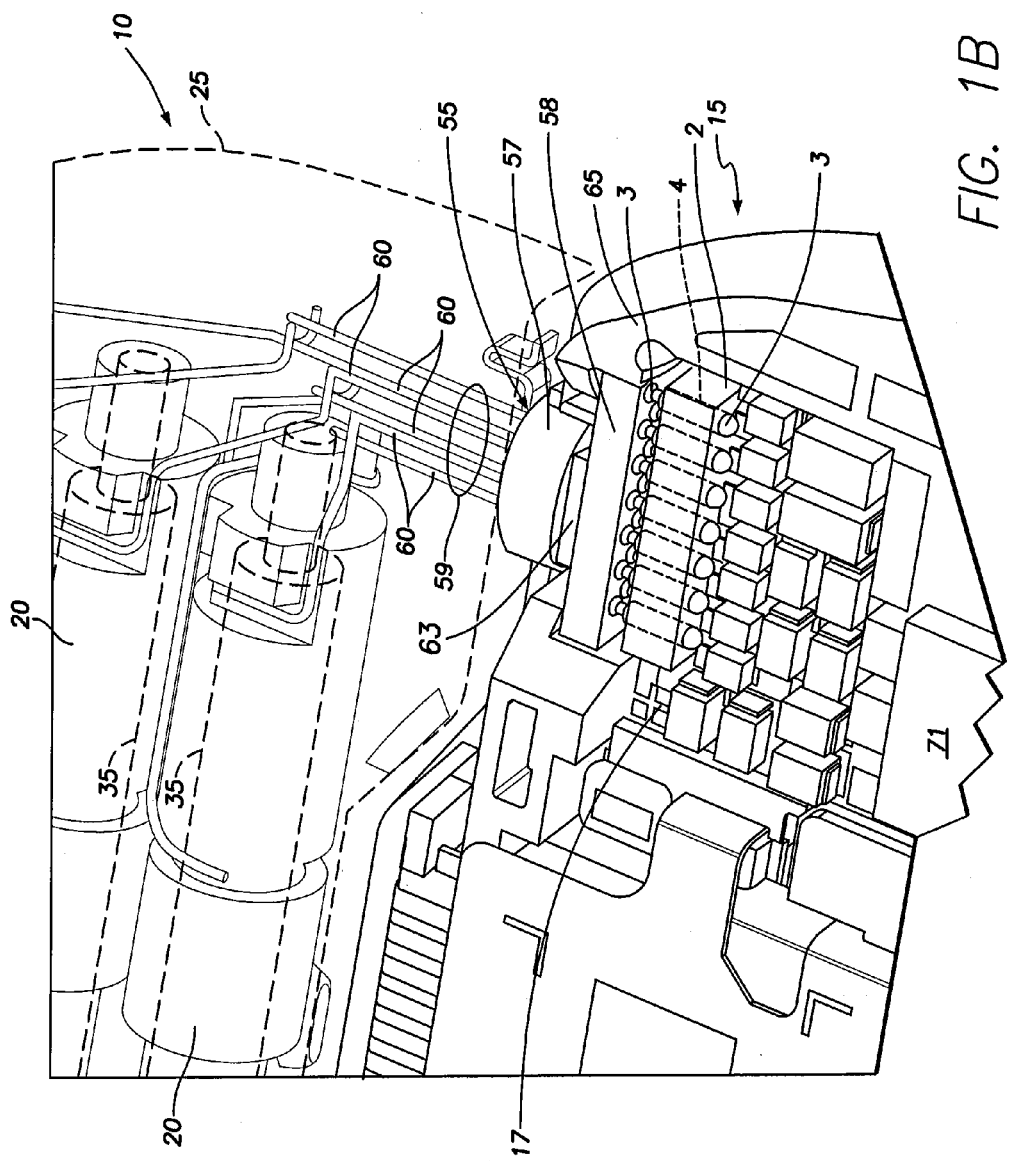
FIG. 1B is a side isometric view of region A of the implantable pulse generator of FIG. 1A, wherein the wall of the can is cut away to show the components of the pulse generator enclosed in the can and the exterior of the header is shown in phantom lines to depict the interior components of the header.

As can be understood from FIGS. 1A and 1B, the present disclosure describes a feedthru assembly 55 of an implantable pulse generator 5 such as, for example, a pacemaker or an ICD. As can be understood from FIGS. 6, 10, 14 and 18, in one embodiment, the feedthru assembly 55 disclosed herein is a feedthru assembly 55 having a grouped or multi-row lead array feedthru 57 close coupled to an electro-magnetic interference ("EMI") filter 63 and an inline lead array feedthru board 58. The feedthru 57 disclosed herein has a grouped or multi-row array 59, and the board 58 has an inline array 61. For purposes of the discussion herein and the attached claims, a grouped, bunched or multi-row array 59 will be any array of feedthru wires 60 arranged in multiple rows, a circular, square, rectangular or oval arrangement, or any other grouped array arrangement that is not comprised of a single row of feedthru wires 60. Also, for purposes of the discussion herein and the attached claims, an inline or linear array 61 will be any array of conductor wires 3 arranged in a single linear row of conductor wires 3.

As will become evident from the following discussion and the attached figures, the feedthru assembly 55 disclosed herein is advantageous in that it offers the compactness of a grouped or multi-row array 59 for the feedthru 57 while offering an inline array 61 for the board 58 that can be simply plugged into a similarly configured plug-type connector 2, thereby providing a simple, robust and compact electrical connection between the feedthru assembly 55 and the electronic component substrate 17 housed in the can 15. Such an arrangement improves ease of manufacture and reduces manufacturing costs.

In some embodiments, the assembly 55 may also include an EMI filter 63 that includes integrated filtering layers imbedded in the body of the filter. The resulting feedthru assembly 55 with its EMI filter 63 is additionally advantageous with respect to compactness, ease of manufacture, and reduced manufacturing costs.

For a general discussion of an implantable pulse generator 5 that utilizes the feedthru assembly 55 having a grouped array feedthru 57 close coupled to a filter 63 and an inline array feedthru board 58, reference is first made to FIGS. 1A and 1B. FIG. 1A is a side view of a pulse generator 5 and an implantable lead 7 positioned to be coupled to the pulse generator. FIG. 1B is a side isometric view of region A of the implantable pulse generator 5 of FIG. 1A, wherein the wall 65 of the can 15 is cut away to show the components of the pulse generator enclosed in the can and the exterior of the header 10 is shown in phantom lines to depict the interior components of the header.

As indicated in FIGS. 1A and 1B, the pulse generator 5 includes a header 10 and a can or housing 15. The header 10 includes connector blocks 20 and a molded portion 25 (shown in solid lines in FIG. 1A and phantom lines in FIG. 1B) that encloses the connector blocks 20. Each connector block 20 includes an opening 35 configured to receive therein and mate with a connector end 40 of a proximal end 45 of an implantable lead 7, thereby forming an electrical connection between the connector block 20 and the lead connector end 40 and mechanically securing the proximal end 45 of the lead 7 to the header 10 of the pulse generator 5.

As illustrated in FIG. 1A, the header molded portion 25 may be formed of a polymer material or epoxy. Passages 50 extend from the exterior of the molded portion 25 to the openings 35 in the connector blocks 2Q provide a pathway for the lead distal ends 40 to pass through the molded portion 25 and enter the openings 35.

As shown in FIG. 1B, the can 15 includes one or more feedthru assemblies 55 mounted in the wall 65 of the can 15. More specifically, the feedthru assembly 55 includes a grouped array feedthru 57 mounted in the can wall 65 and close coupled to a filter 63 and an inline array feedthru board 58 on a can side of the feedthru 57, thereby forming an integrated feedthru/filter/board assembly 55 that converts the grouped array 59 of the feedthru 57 to an inline array 61 of the board 58. Each individual conductor wire 3 that is part of the linear array 61 is received in a corresponding contact hole 4 of a connector 2 that is electrically coupled to the electronic components 71 (e.g., hybrid, or various other electronic components), which are mounted on, and electrically interconnected via, an electronic substrate 17, all of which are housed within the can 15. Thus, the linear array 61 is configured to be plugged into the linear array of contact holes 4 of the connector 2. Accordingly, the feedthru assembly 55 is configured to provide a grouped array 59 of feedthru wires 60 for coupling to the connector blocks of the header while providing a linear array 61 of conductor wires 3 that can be simply plugged into a similar linear array of holes 4 of a plug-in style connector 2.

As depicted in FIG. 1B, the grouped array 59 includes multiple conductors 60 (e.g., round wires, flat ribbon wires, flex cables or etc.) extending from the header side of the feedthru 57 to respective connector blocks 20. As will be discussed in detail below, the multiple conductors 60 of the bunched array 59 on the can side of the feedthru 57 are wires 60 and are received in a bunched array of connector holes in the board 58, which has conductors (e.g., traces, wires, etc.) that extend through the body of the board 58 to respective wires 3 of the linear array 61.

The can 15 provides a hermetically sealed enclosure for the pulse generator's electronic components 71 (e.g., hybrid, or various other electronic components), which are mounted on, and electrically interconnected via, an electronic substrate 17, all of which are housed within the can 15. As mentioned above, the linear array 61 of wire conductors 3 are received in the contact holes 4 that are arranged in a complementary and matching linear array of contact holes 4 in the connector 2. Electrical conductors (e.g., in the form of wires, cables, wire bonds, traces, welds, solders, etc.) electrically couple the contact holes 4 to the electrical circuits of the electronic substrate 17, and, as a result, to the electronic components 71. Typically, the wall of the can 15 is made of titanium or another biocompatible metal.

For a detailed discussion of the components of the feedthru 57, reference is now made to FIGS. 2-5. FIGS. 2-5 are, respectively, top side isometric, side, end, and bottom side isometric views of an embodiment of the feedthru 57 of feedthru assembly 55 shown in FIG. 1B.

Figure 2:
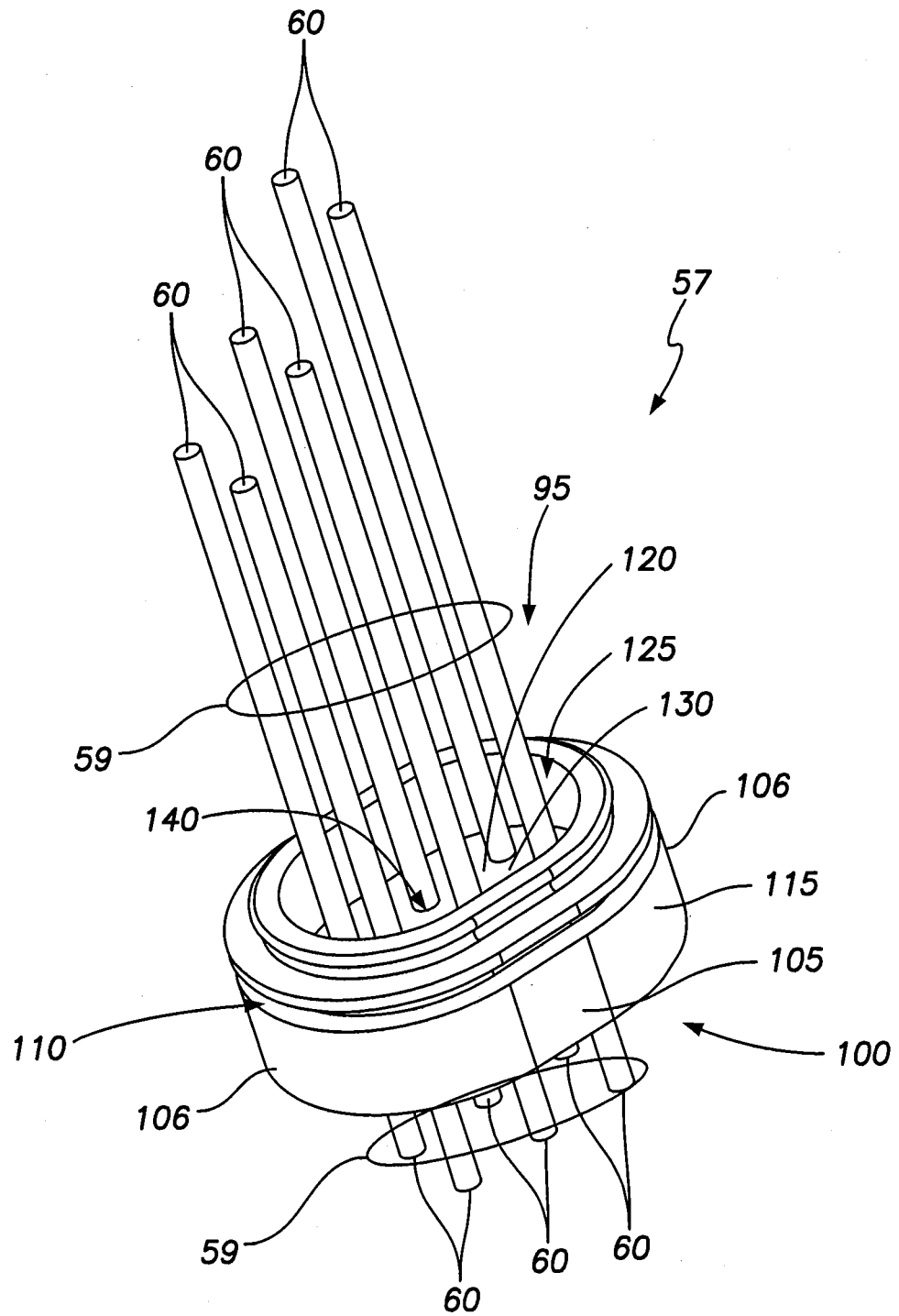
FIG. 2 is a top side isometric view of the feedthru of the feedthru assembly depicted in FIG. 1.
Figure 3:
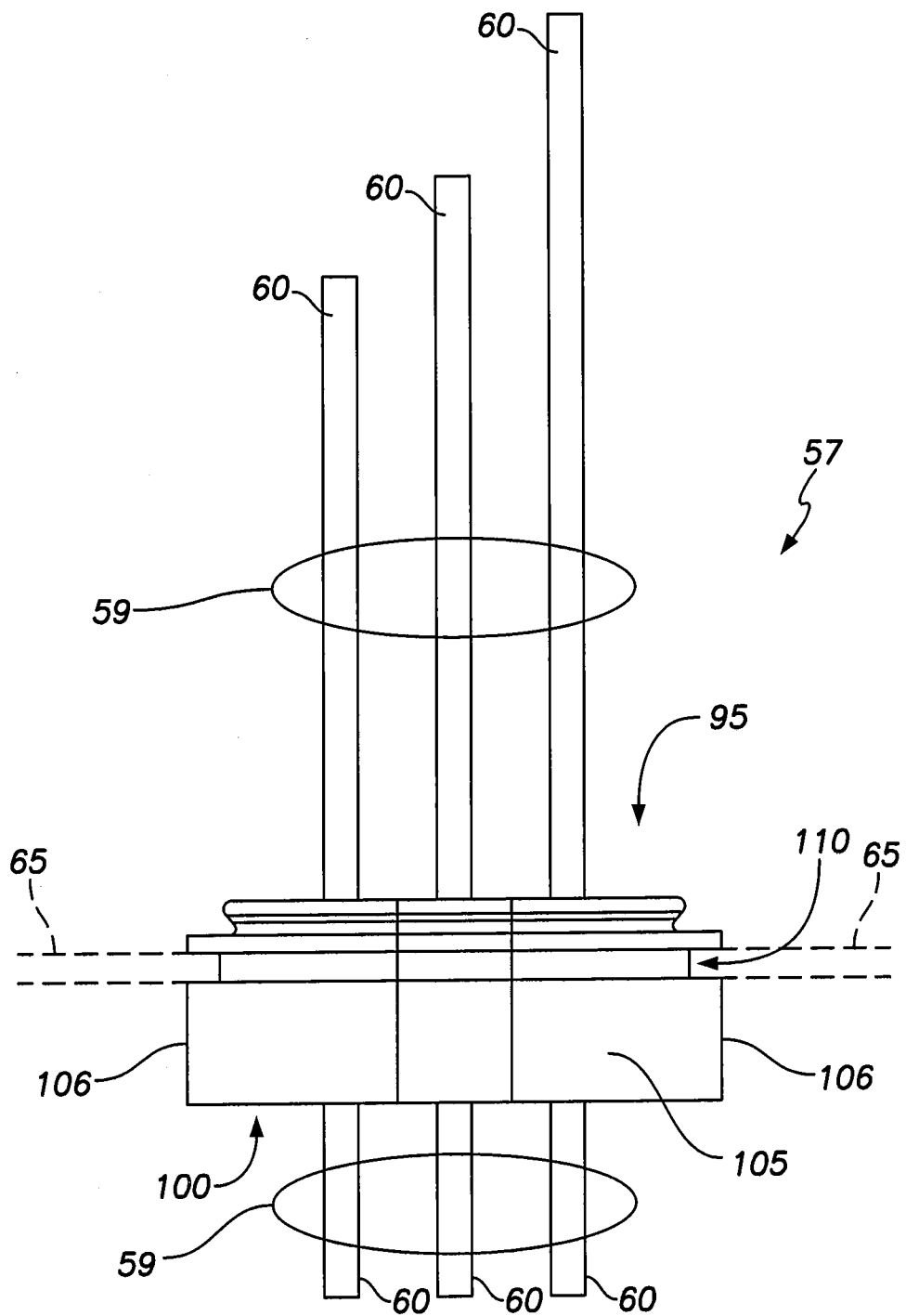
FIG. 3 is a side view of the feedthru.
Figure 4:
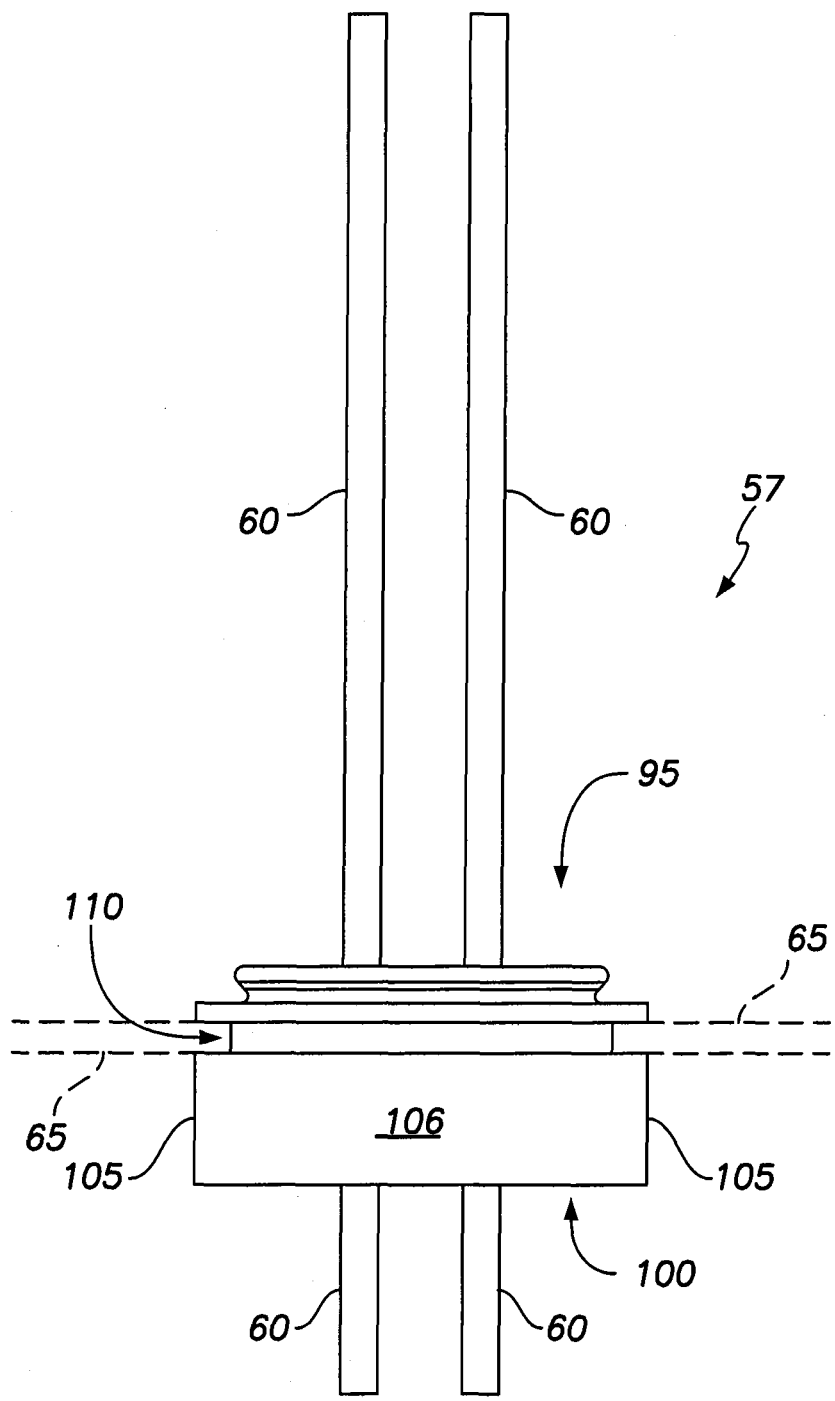
FIG. 4 is an end view of the feedthru.

In one embodiment, as shown in FIGS. 2-5, the feedthru 57 includes a header side 95, a can side 100, opposed longitudinally extending sides 105, and opposed ends 106. While the overall shape of the feedthru 57 depicted in FIGS. 2-4 is generally oval, in other embodiments the overall shape of the feedthru 57 may be other shapes, including rectangular, square, circular, etc.

As can be understood from FIGS. 2-5, the feedthru 57 includes a feedthru housing 115, a core 120, and feedthru conductors 60, which may be in the form of solid cylindrical wires or other types of conductor configurations. The feedthru housing 115 forms the sides 105 and ends 106 of the feedthru 57 and includes a central or core-receiving opening 125. The feedthru housing 115 may be machined, molded or otherwise formed to fit the space and design constraints of an implantable pulse generator 5. The feedthru housing 115 may be titanium, a titanium alloy, MP35N, or stainless steel. The sides 105 and ends 106 of the feedthru housing 115 may be configured such that a groove or slot 110 is defined therein. As can indicated in FIGS. 3 and 4, the groove or slot 110 in the feedthru housing 115 receives the can wall 65 when the feedthru 57 is mounted in the can wall 65 as shown in FIG. 1B.

Figure 5:
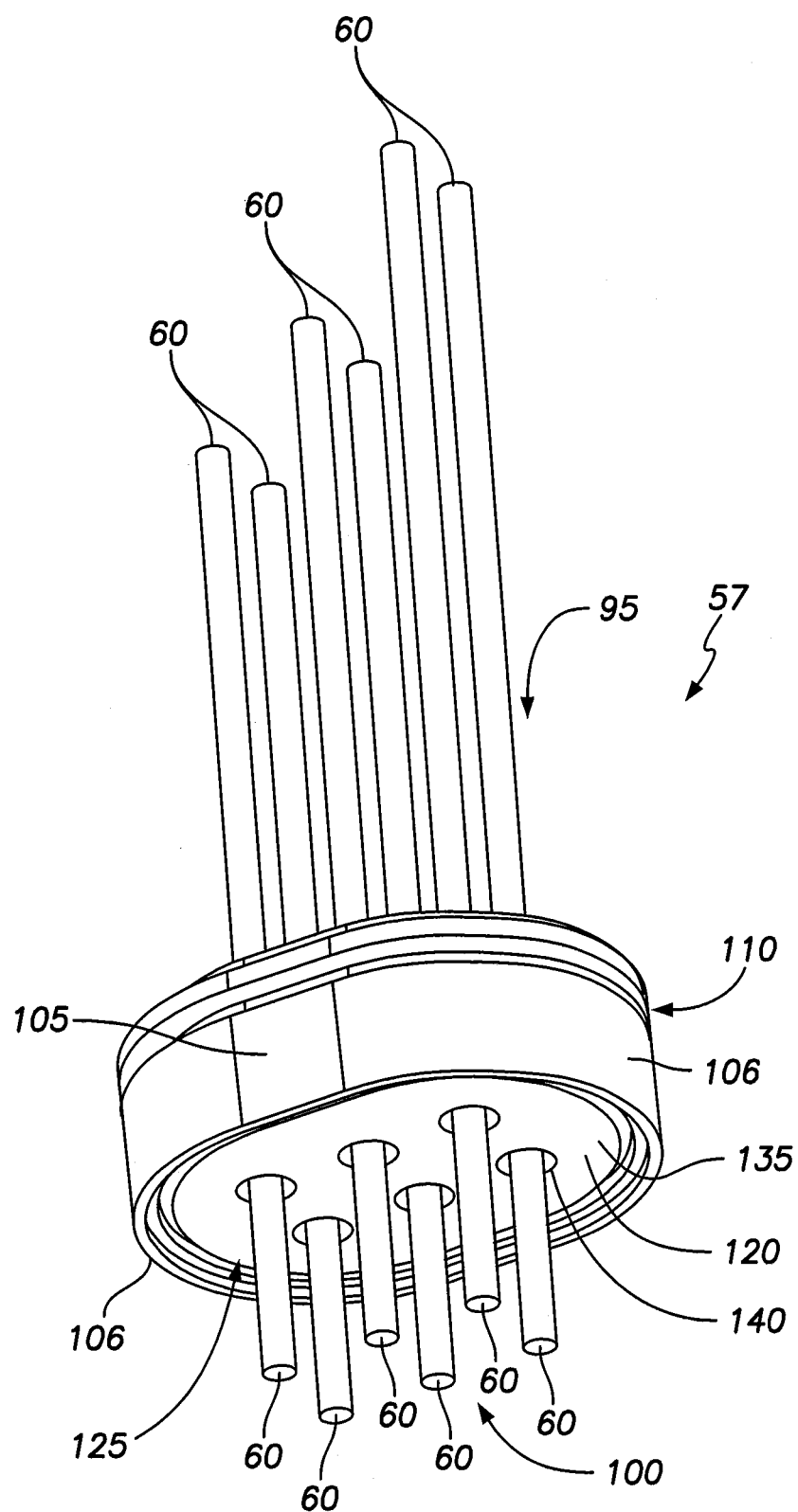
FIG. 5 is a bottom side isometric view of the feedthru.

As can be understood from FIGS. 2 and 5, the central opening 125 of the feedthru housing 115 extends axially through the feedthru housing and defines a void that is occupied by the core 120. The core 120 includes a header face 130, a can face 135, and through-holes 140 extending axially therethrough. The feedthru wires 60 extend through the core 120 via the through-holes 140. The core 120 may be formed of an electrically insulating material, such as ceramic, glass, or sapphire.

As indicated in FIGS. 2-4, there may be six feedthru wires 60 extending through the core 120 in a bunched or grouped array 59 of two rows of three wires 60 (e.g., a hex pattern). In other embodiments, the wires 60 may be of a greater or lesser number and configured in other multi-rowed, bunched or grouped arrangements. For example, there may be four feedthru wires 60 it two rows of two wires 60 (e.g., a quad pattern). Such grouped or bunched arrays 59 are more compact as compared to an array having a linear, single line of multiple feedthru wires (e.g., a single row of six feedthru wires or a single line of four feedthru wires as respectively compared to the aforementioned hex pattern and quad pattern grouped arrangements).

The feedthru wires 60 may be made of gold, platinum, nickel, titanium, or MP35N. To assemble the feedthru 57, the feedthru housing 115 and core 120 may be connected by soldering, brazing, welding or other suitable method to form a feedthru housing-core assembly. The coupling of the core 120 to the feedthru housing 115 creates a hermetic seal. The feedthru wires 60 may be connected to the holes 140 of the core 120 by brazing, soldering, welding or other suitable method.

Figure 6:
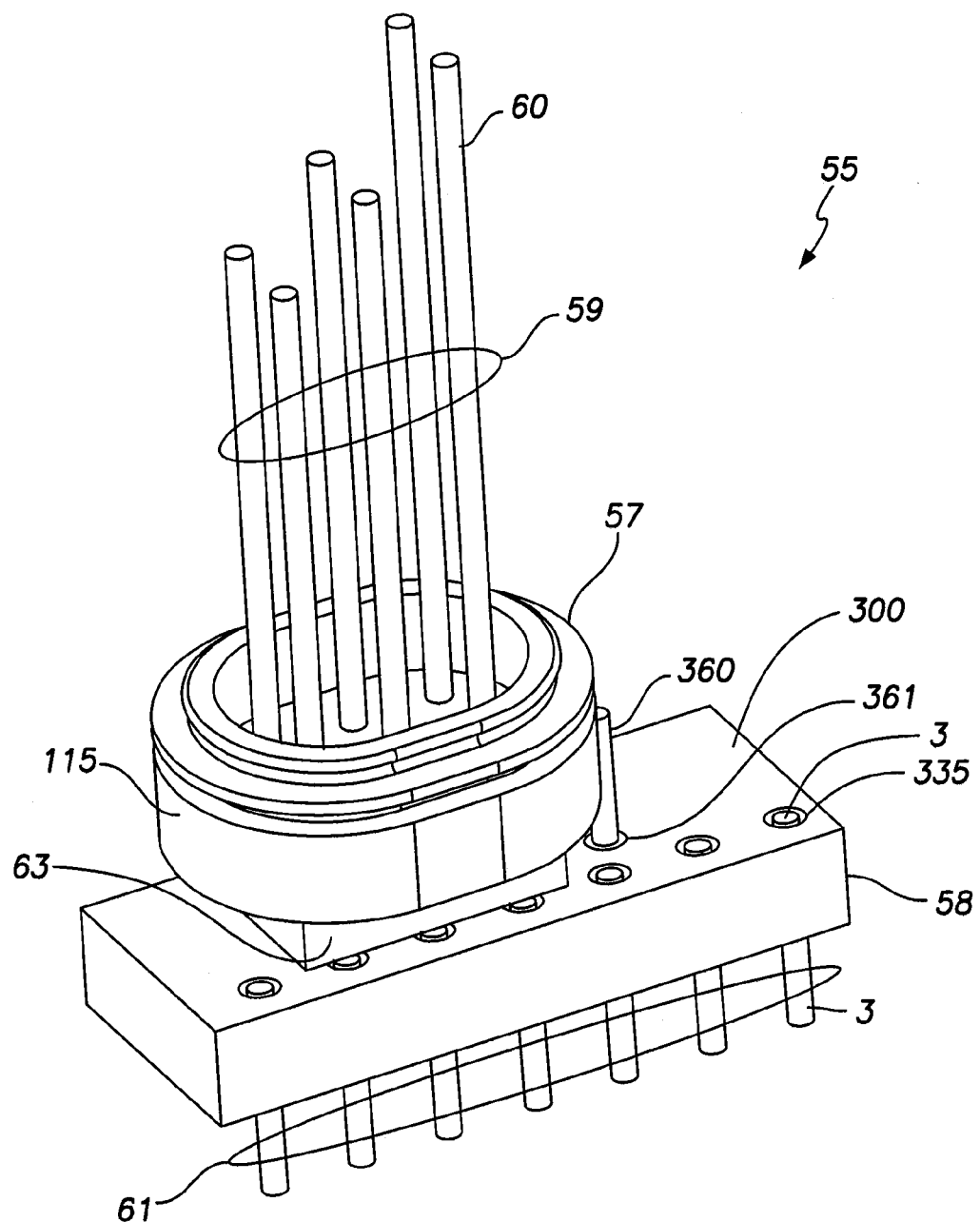
FIG. 6 is a top side isometric view of the feedthru assembly depicted in FIG. 1A, wherein the feedthru assembly includes the feedthru of FIG. 2 and an integrated or close coupled filter and an inline lead array feedthru board.
Figure 7:
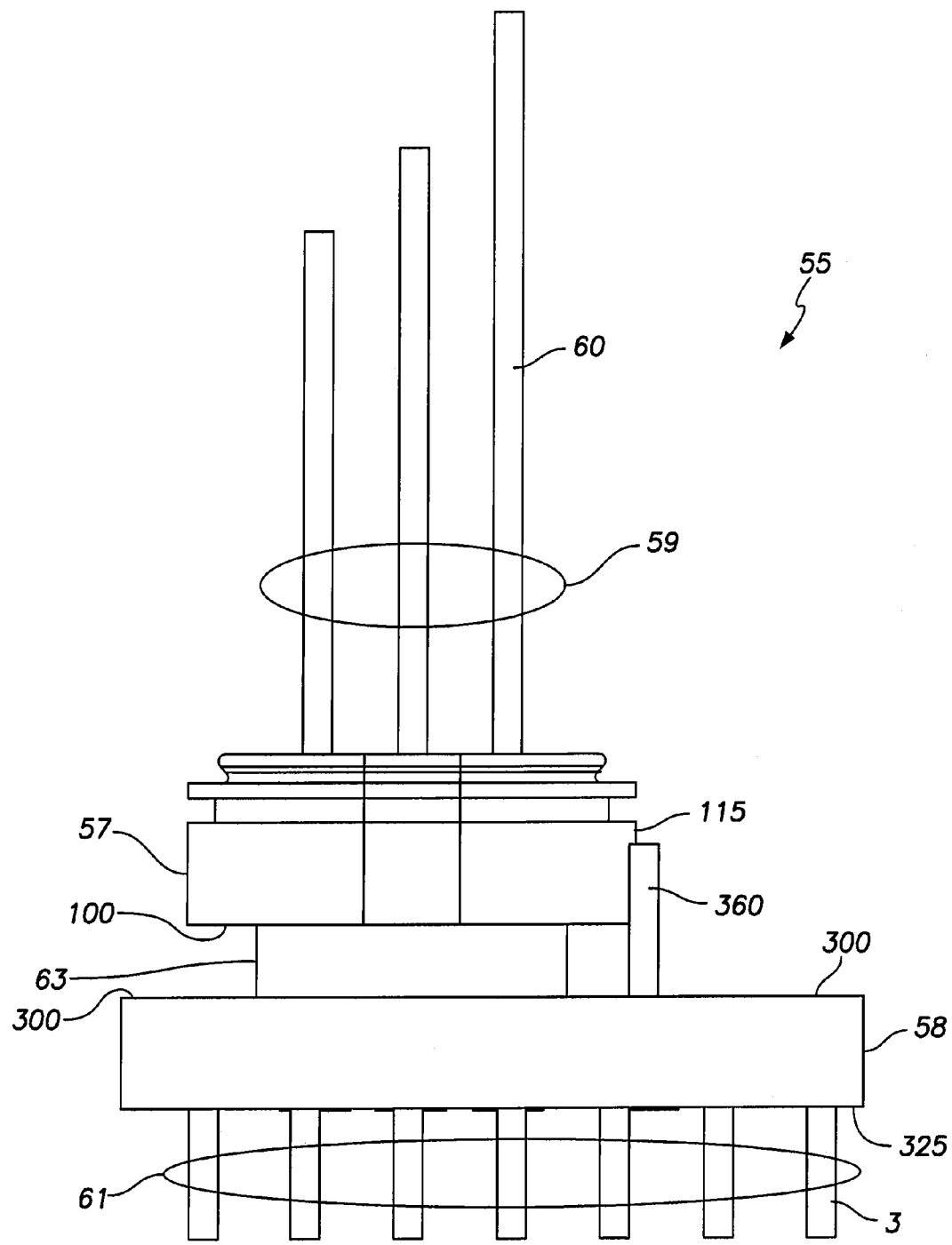
FIG. 7 is a side view of the linear array side of the feedthru assembly.
Figure 8A:
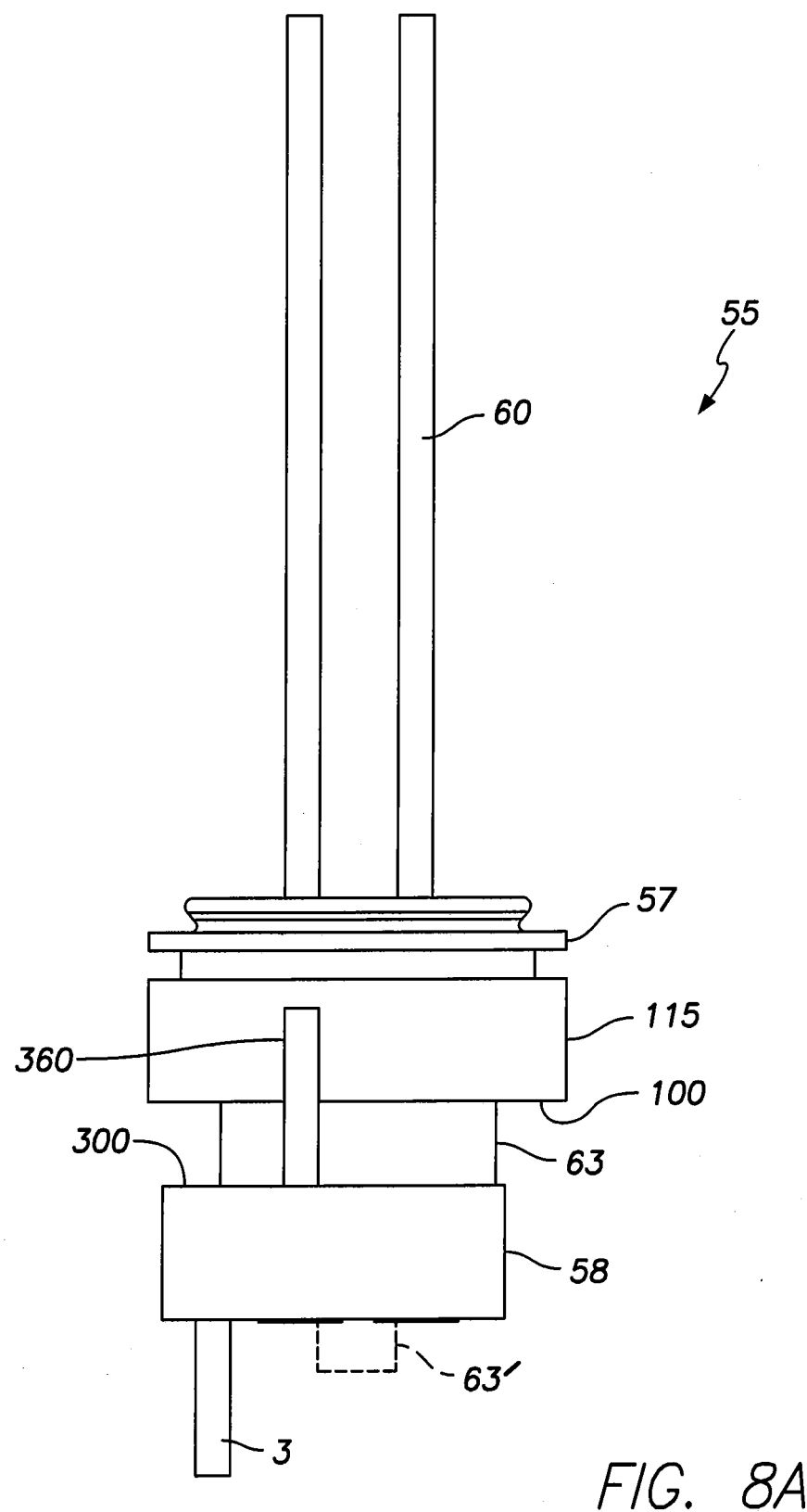
FIGS. 8A and 8B are opposite end views of the feedthru assembly.
Figure 8B:
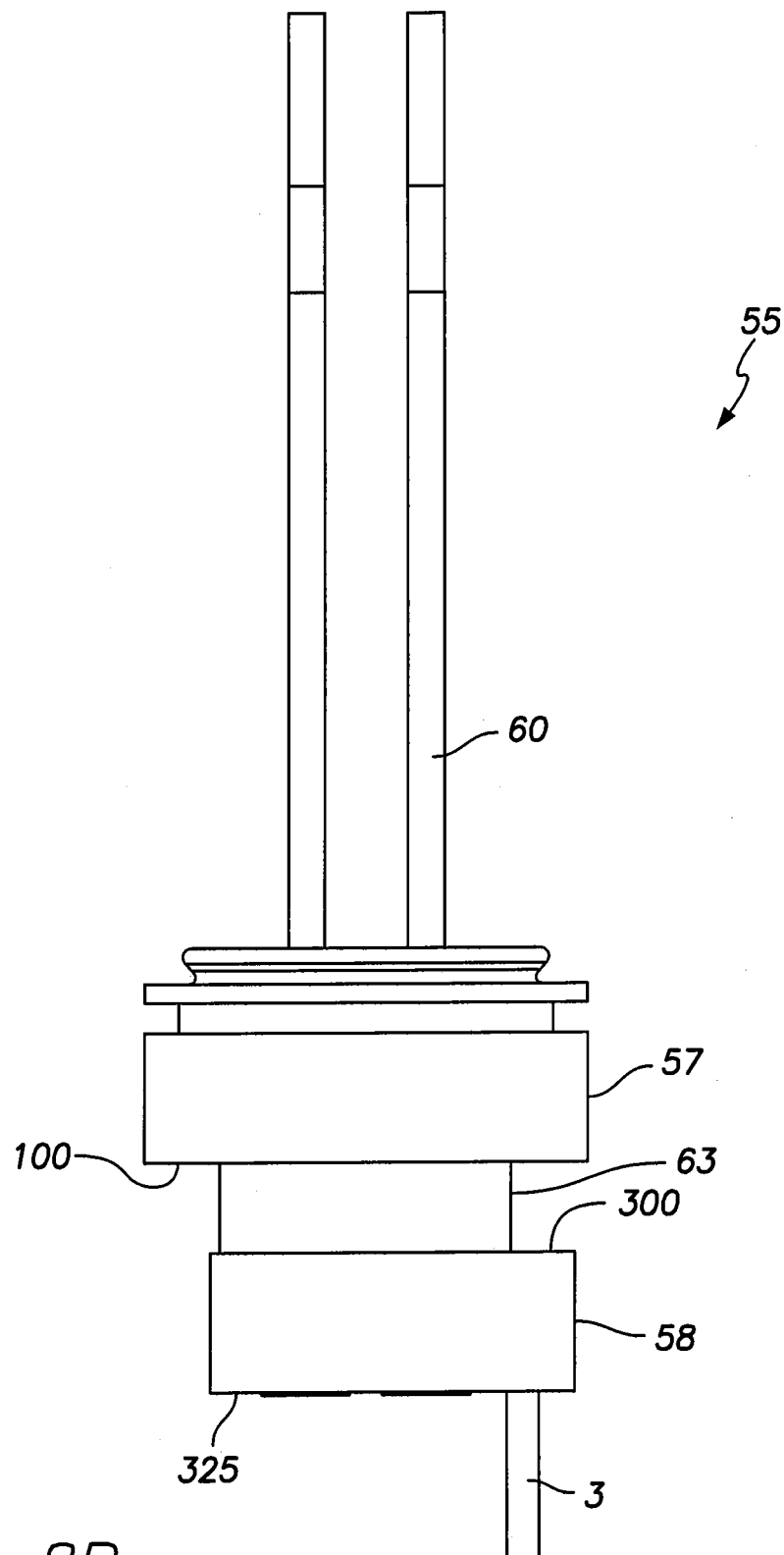
Figure 9:
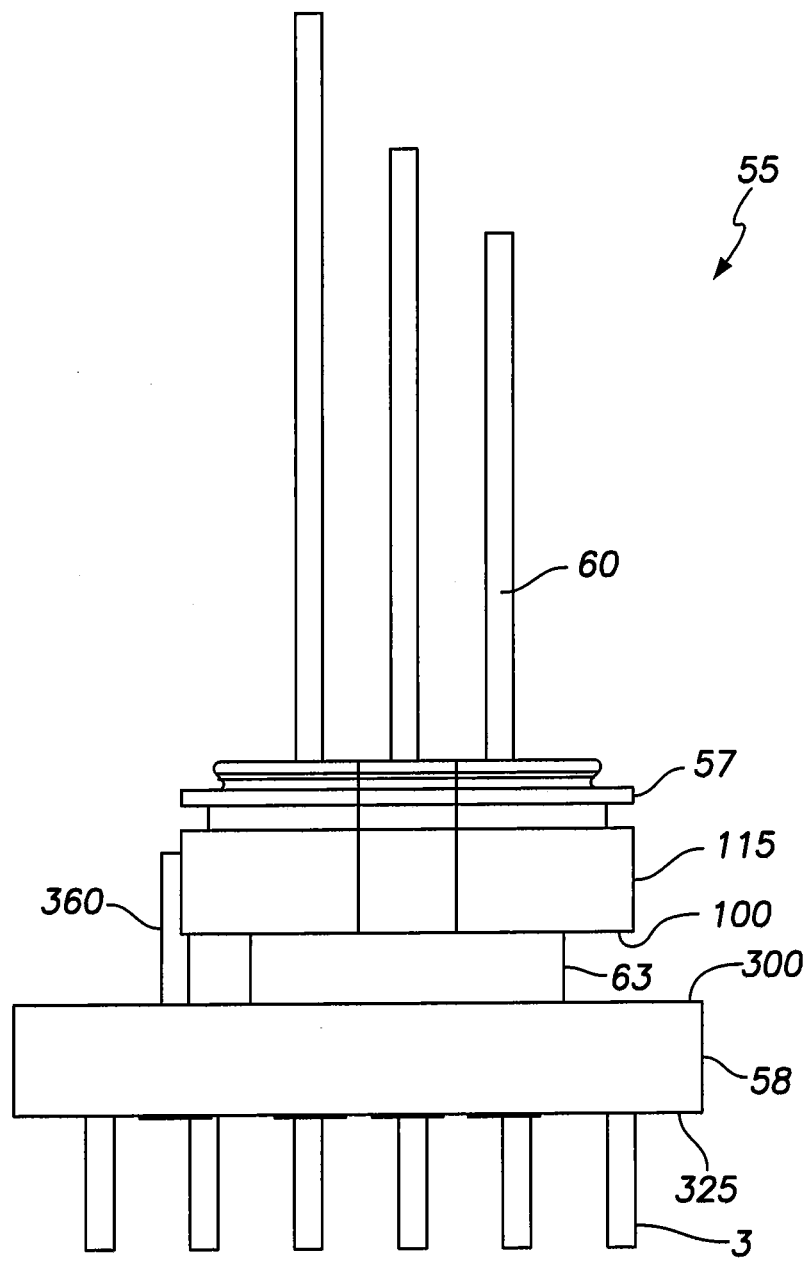
FIG. 9 is a side view of the feedthru assembly opposite the side depicted in FIG. 7.
Figure 10:
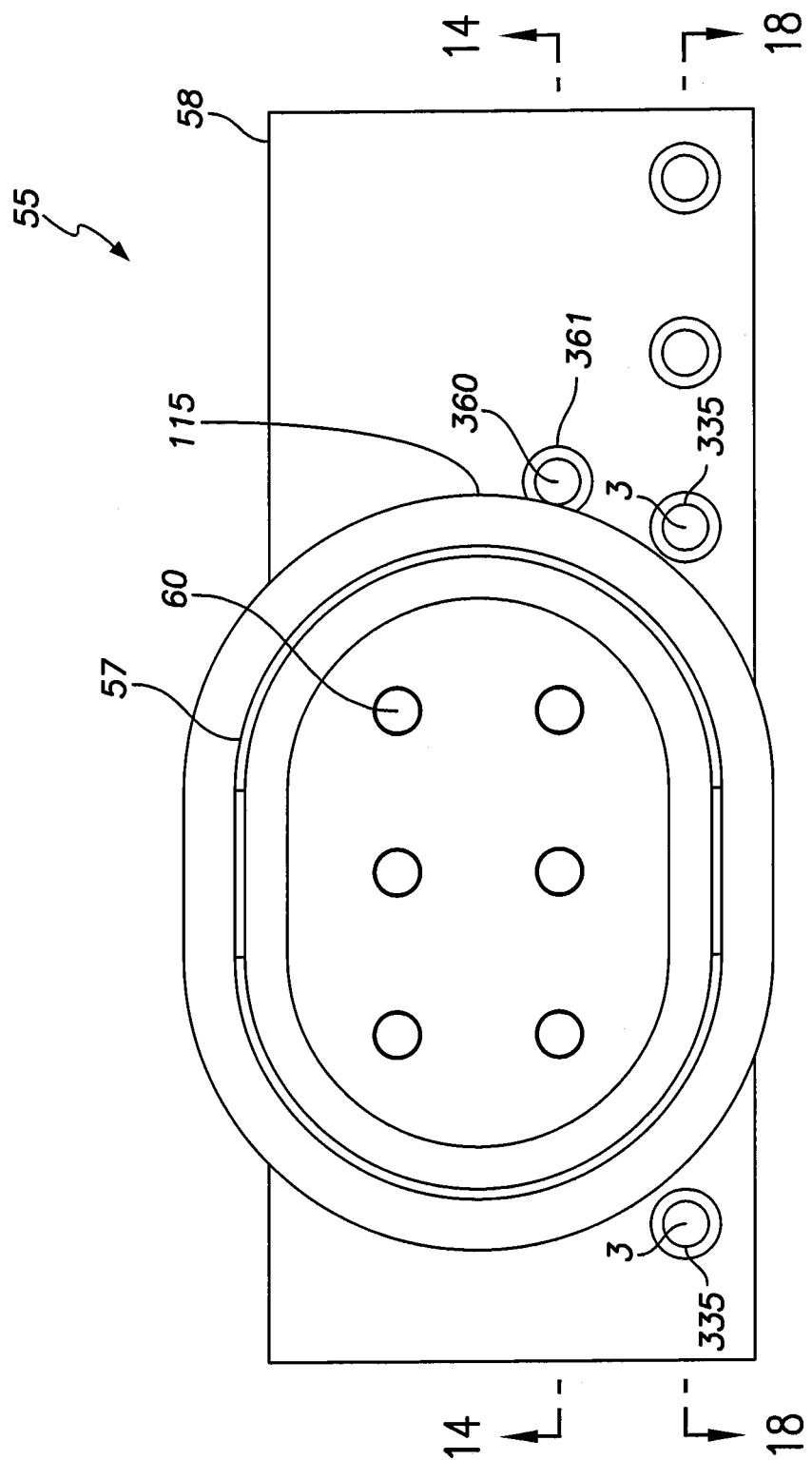
FIG. 10 is a top plan view of the feedthru assembly.
Figure 11:
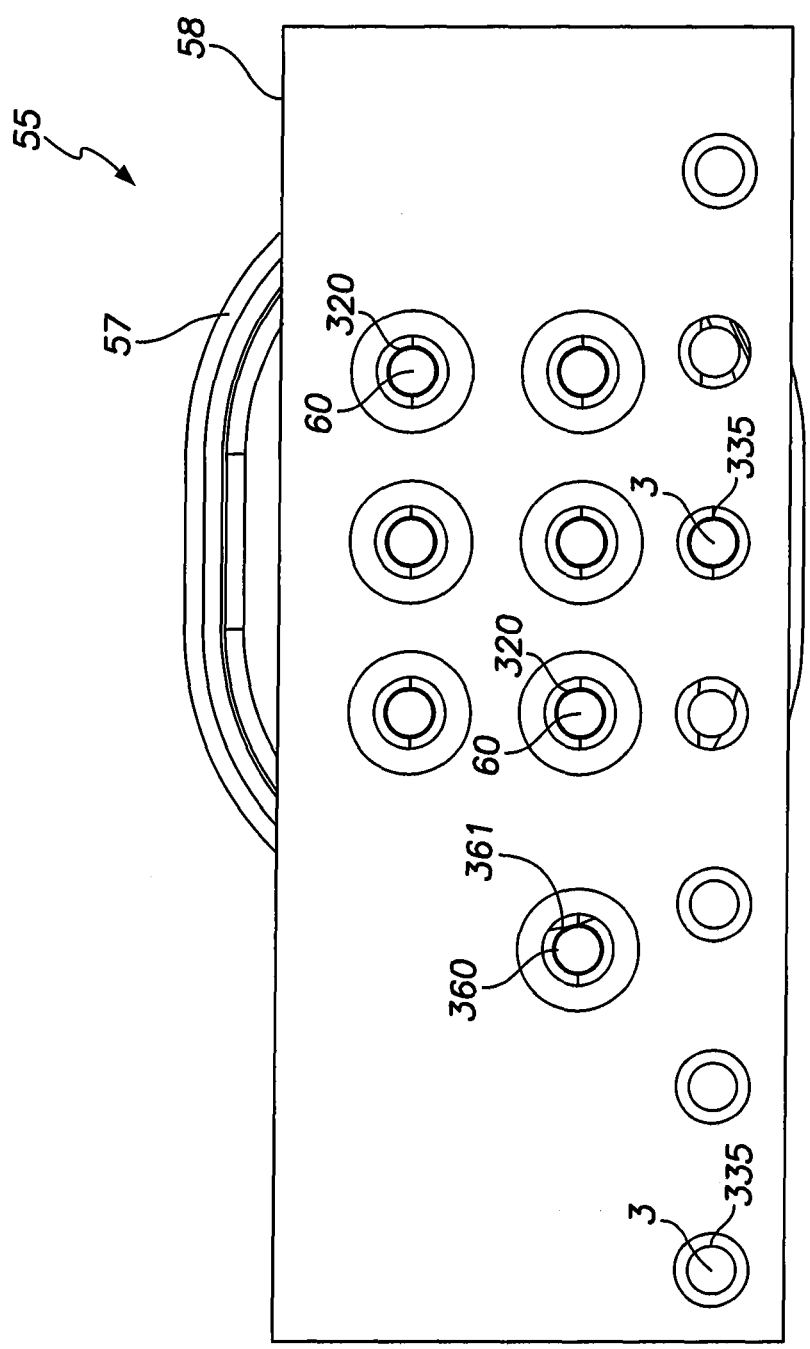
FIG. 11 is a bottom plan view of the feedthru assembly.
Figure 14:
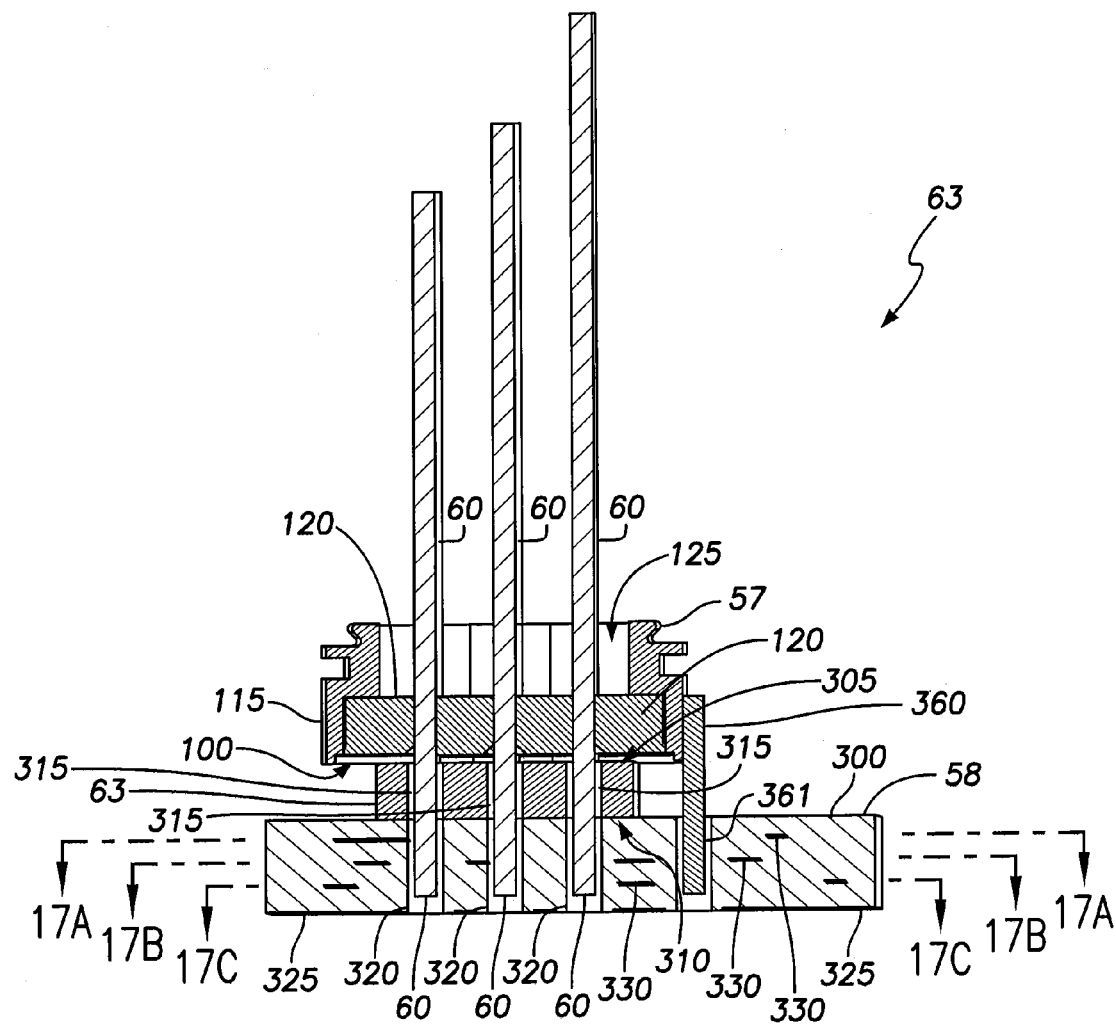
FIG. 14 is a cross-section side view of the feedthru assembly as taken along section line 14-14 in FIG. 10.

For a discussion regarding the feedthru assembly 55 including the grouped array feedthru 57 integrated or close coupled with the EMI filter 63 and an inline array feedthru board 58, reference is made to FIGS. 6-11. FIG. 6 is a top side isometric view of the feedthru assembly 55 shown in FIG. 1B. FIGS. 7-10 are various side, end and plan views of the feedthru assembly 55. As illustrated in FIGS. 6-10, the feedthru 57, filter 63 and board 58 are generally sandwiched together in a close coupled arrangement. Specifically, as indicated in FIG. 14, the filter 63 is sandwiched together between a can side 100 of the feedthru 57 and a filter side 300 of the board 58. A feedthru side 305 of the filter 63 abuts against the can side 100 of the feedthru 57, and a board side 310 of the filter 63 abuts against the filter side 300 of the board 58.

While the EMI filter 63 is shown in FIGS. 6-9 as being located between the feedthru 57 and the board 58 and, further as discussed below, having a layered configuration, in other embodiments the EMI filter 63 may be located elsewhere and have other configurations. For example, in one embodiment, the EMI filter may be in the form of discoidal capacitors located within the housing 115 of the feedthru 57 or on the can side of the feedthru housing 115. As indicated in FIG. 8A via dashed lines, in one embodiment, the EMI filter 63' may be discrete capacitors 63' supported off of the feedthru assembly 55 somewhere, such as, the bottom surface of the board 58.

Figure 12:
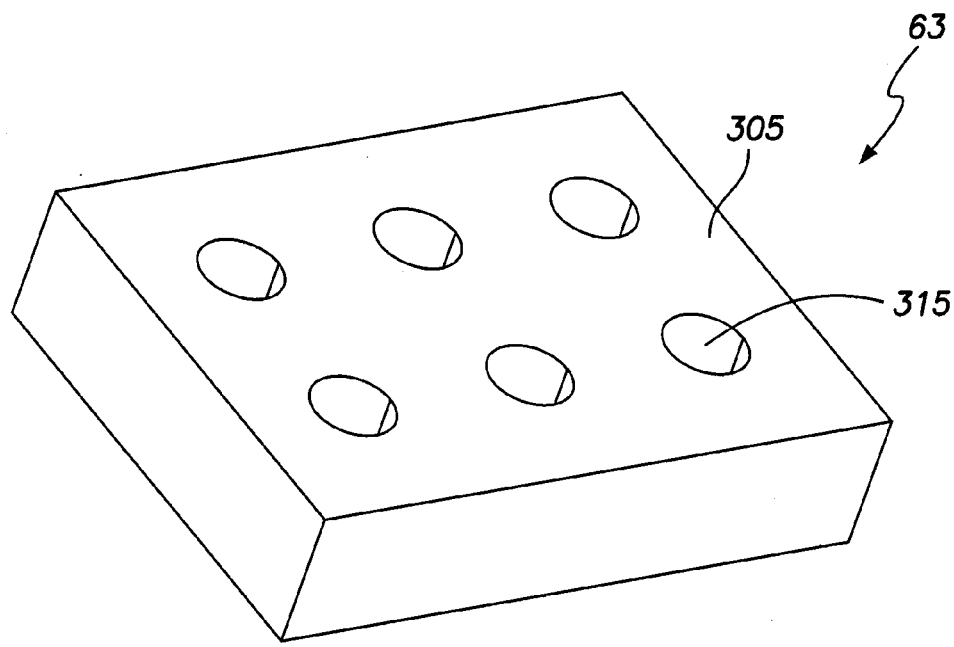
FIGS. 12 and 13 are, respectively, feedthru side isometric and board side isometric views of the EMI filter.
Figure 13:
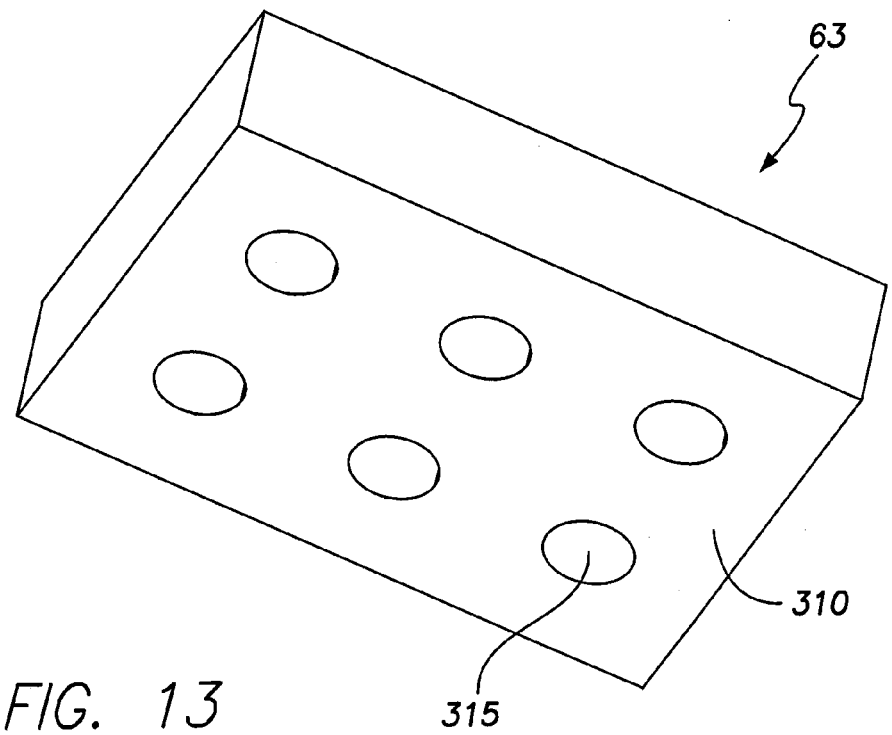

As illustrated in FIGS. 12 and 13, which are, respectively, feedthru side isometric and board side isometric views of the filter 63, the filter may be a generally rectangular box shape through which via holes 315 extend between the feedthru side 305 and board side 310 to daylight at each side. As can be understood from a comparison of FIGS. 10 and 12, the via holes 315 are arranged in the same double row, grouped arrangement with the same spacing as the feedthru wires 60 of the feedthru 57. Thus, as can be understood from FIG. 14, which is a cross-section side view of the feedthru assembly 55 as taken along section line 14-14 in FIG. 10, each feedthru wire 60 extends down into and through a respective via hole 315 of the filter 63.

The surfaces of the via holes 315 are coated with an electrically conductive material, such as gold, nickel, platinum, etc., where such coating is provided via electroplating, photo deposition, vapor deposition, etc. As a result of the electrically conductive coating of the via holes, each feedthru wire 60 is in electrical contact with the electrically conductive coating of its respective via hole 315. The via holes 315 are used to electrically couple together capacitance layers, which are separated by associated insulation layers, and imbedded in the body of the filter such that the filter 63 forms an EMI filter 63. As a result, each feedthru wire 60 is electrically coupled to an EMI filtering layer or layers. More detail regarding a layered arrangement of capacitance layers for an EMI filter 63 is given in U.S. patent application Ser. No. 12/607,893, filed Oct. 28, 2009, and is incorporated by reference in its entirety into the present Detailed Description. In other embodiments and instead of employing a layered arrangement of capacitance layers, the EMI filter 63 may employ a series of discrete capacitors within the confines of the boundaries of the filter 63.

By employing the EMI filter 63, the feedthru 57 may be a non-EMI filtered feedthru 57. In the context of this Detailed Discussion, a non-EMI filtered feedthru 57 means a standard feedthru 57 that does not have an integral EMI filter located within its feedthru housing 115 or forming all or part of its core 120. For example, the non-EMI filtered feedthru 57 does not include a discoidal EMI filter or other type of EMI filter forming all or part of the core 120 of the feedthru 57. Instead, the feedthru 57, which has no integral EMI filter capability of its own, is close-coupled with the EMI filter 63 depicted in the attached figures to provide a filtered feedthru assembly 55, the EMI filter capability of the feedthru assembly 55 being integral to the filter 63 sandwiched between the feedthru 57 and board 58. As a result, the non-EMI filtered feedthru 57 is less expensive and more readily available as compared to, for example, an EMI filtered feedthru having an integral discoidal filter.

In another embodiment, the filter 63 can be eliminated with the use of an EMI filtered feedthru 57. In such an embodiment, the feedthru 57 can be directly close coupled to the board 58 such that the can side 100 of the feedthru generally abuts against the top side 300 of the board 58.

Figure 15:
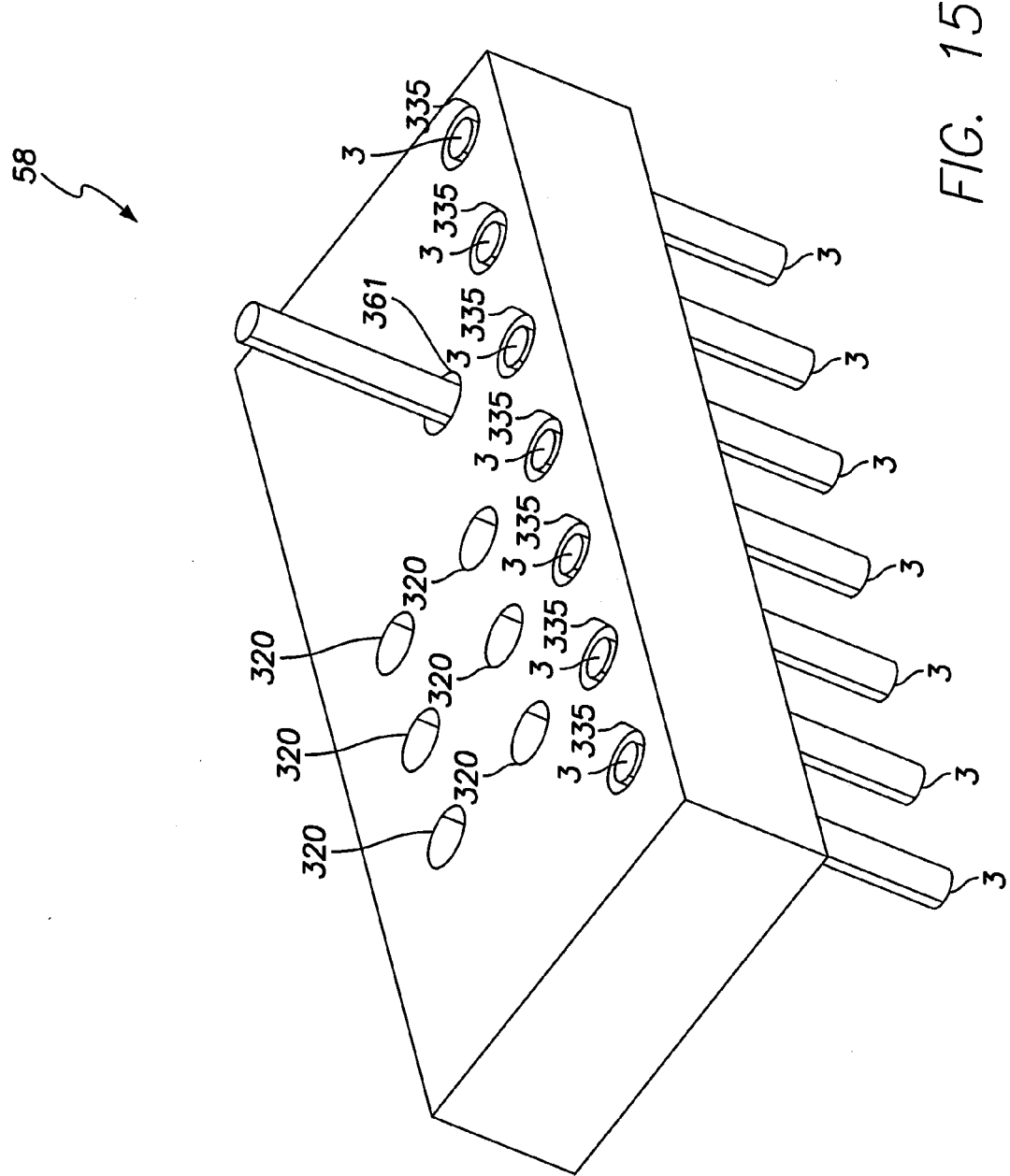
FIGS. 15 and 16 are, respectively, filter side isometric and an opposite side isometric views of the board.
Figure 16:
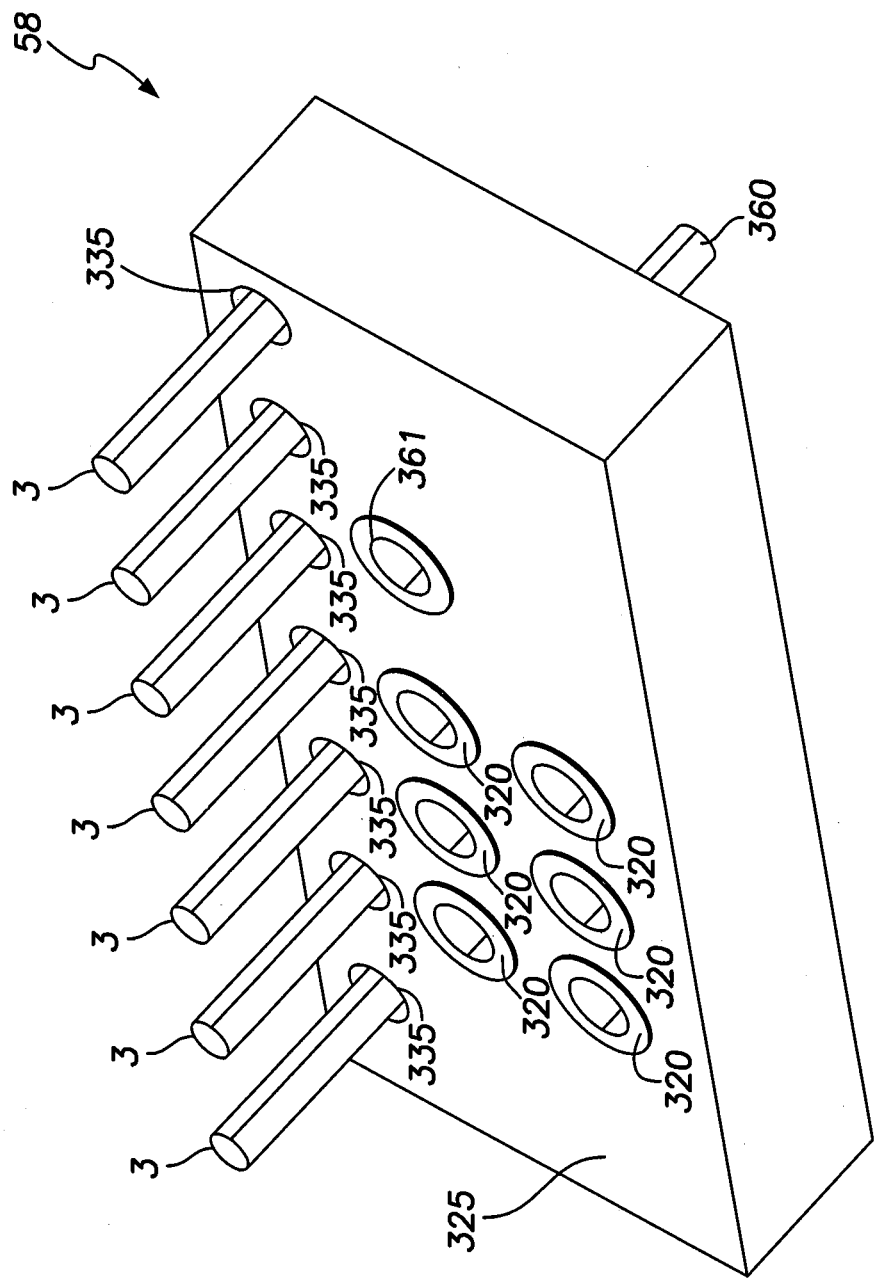

As illustrated in FIGS. 15 and 16, which are, respectively, filter side isometric and an opposite side isometric views of the board 58, the board 58 may be a generally rectangular box shape through which via holes 320, 335 extend between the filter side 300 and opposite side 325 to daylight at each side. As can be understood from a comparison of FIGS. 10 and 15, the via holes 320 are arranged in the same grouped, double row arrangement with the same spacing as the feedthru wires 60 of the feedthru 57. Thus, as can be understood from FIG. 14, each feedthru wire 60 extends down through a respective via hole 315 of the filter 63 and into a respective via hole 320 of the board 58.

Figure 18:
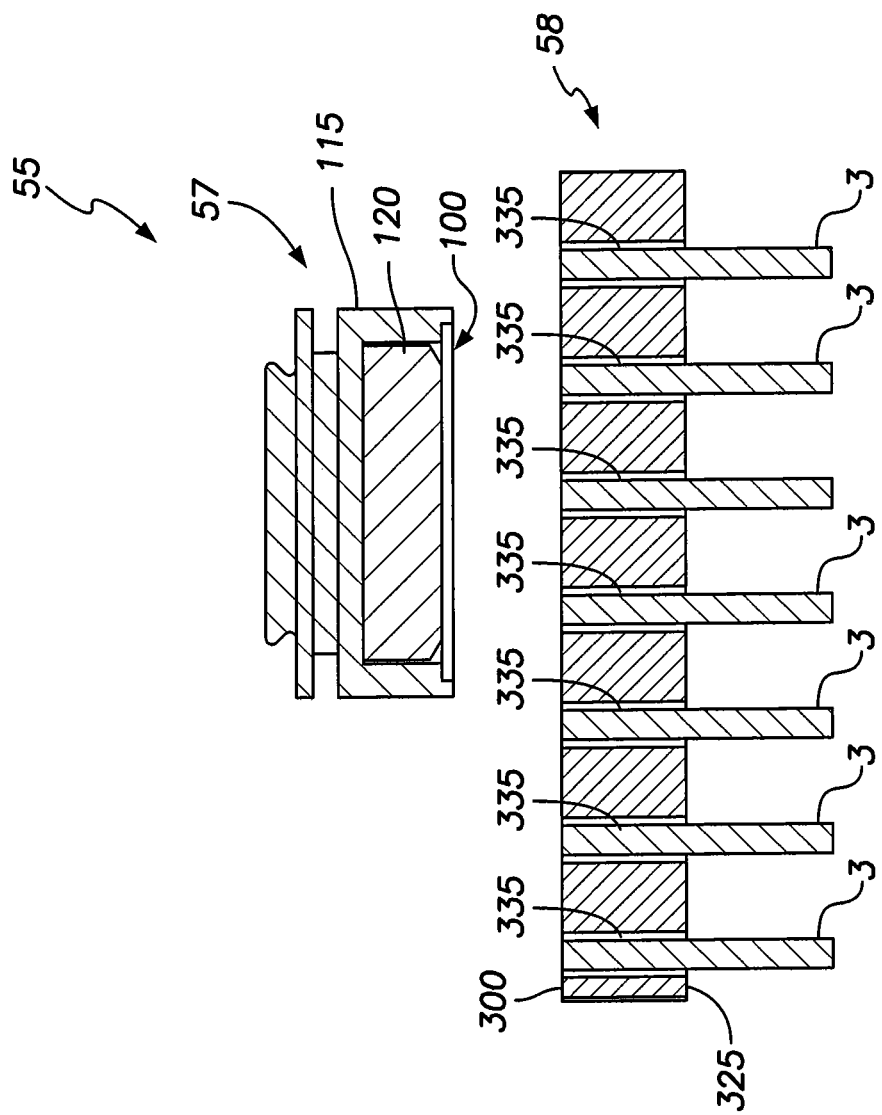
FIG. 18 is a cross-section side view of the feedthru assembly as taken along section line 18-18 in FIG. 10.

As can be understood from FIG. 15, the other via holes 335 are arranged in a single linear line. As illustrated in FIGS. 15 and 18, each via hole 335 is occupied by a wire 3 of the linear array 61. Also, a ground wire 360 extends out of a via hole 361 defined in the body of the board 58, the upper portion of the ground wire 361 making electrical contact with the feedthru housing 115, as can understood from FIG. 10. The wires 3, 361 may be made of gold, platinum, nickel, titanium, or MP35N.

The surfaces of the via holes 320, 335, 361 of the board 58 are coated with an electrically conductive material, such as gold, nickel, platinum, etc., where such coating is provided via electroplating, photo deposition, vapor deposition, etc. As a result of the electrically conductive coating of the via holes, each feedthru wire 60, each linear array wire 3, and the ground wire 360 is in electrical contact with the electrically conductive coating of its respective via hole 320, 335, 361.

Figure 17A:
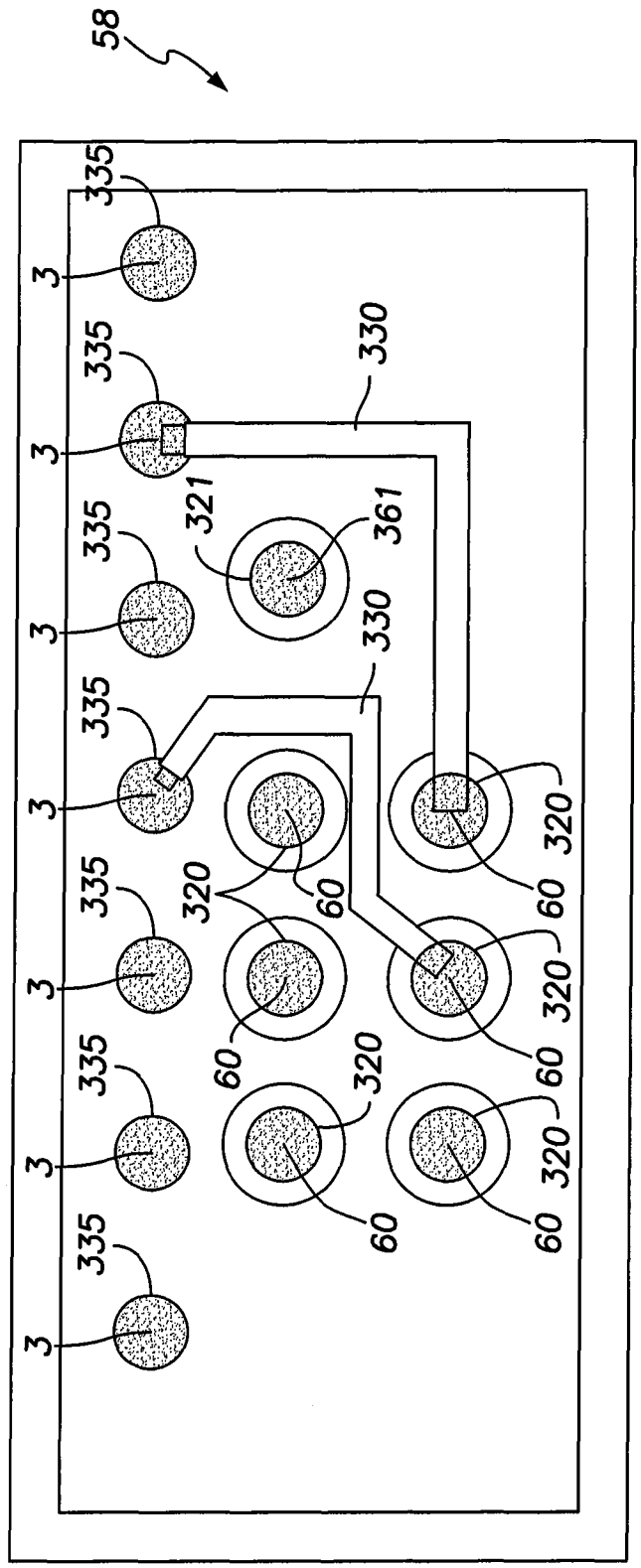
FIGS. 17A-17C are, respectively, plan view cross sections taken along section lines 17A-17A, 17B-17B and 17C-17C in FIG. 14.
Figure 17B:
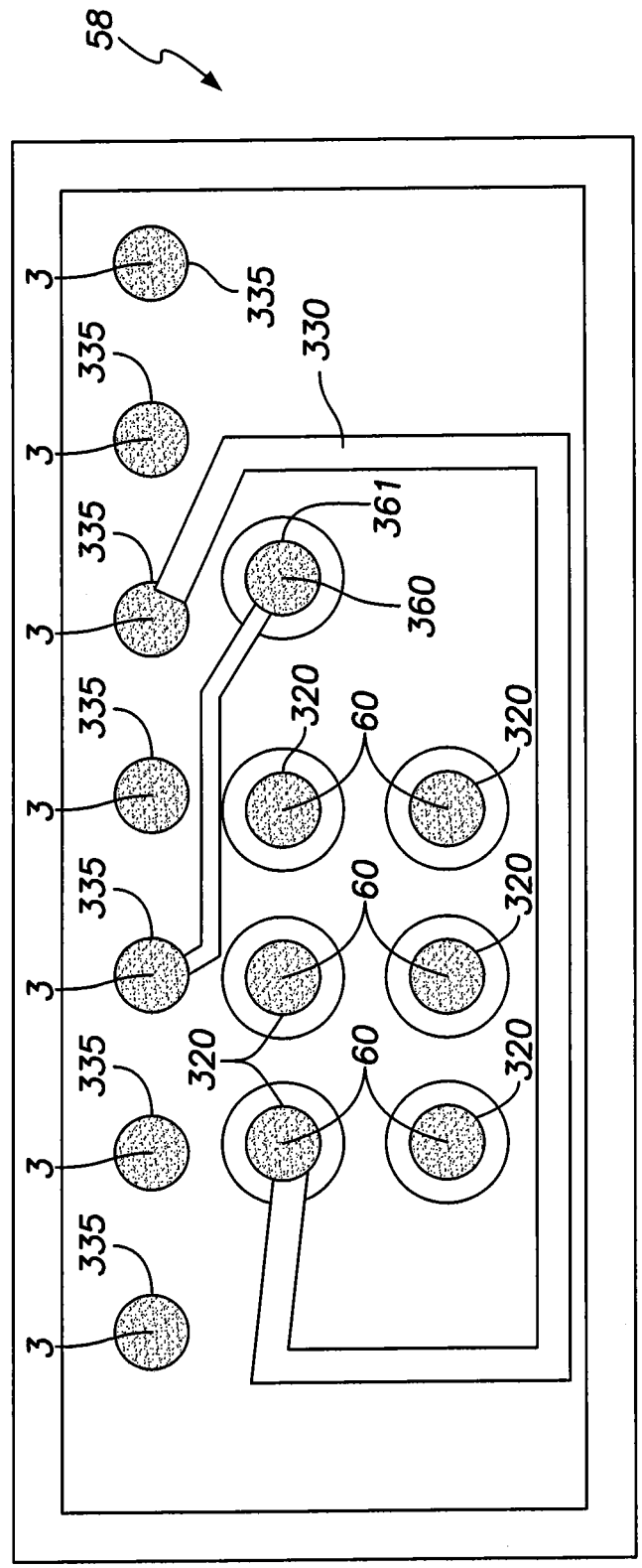
Figure 17C:
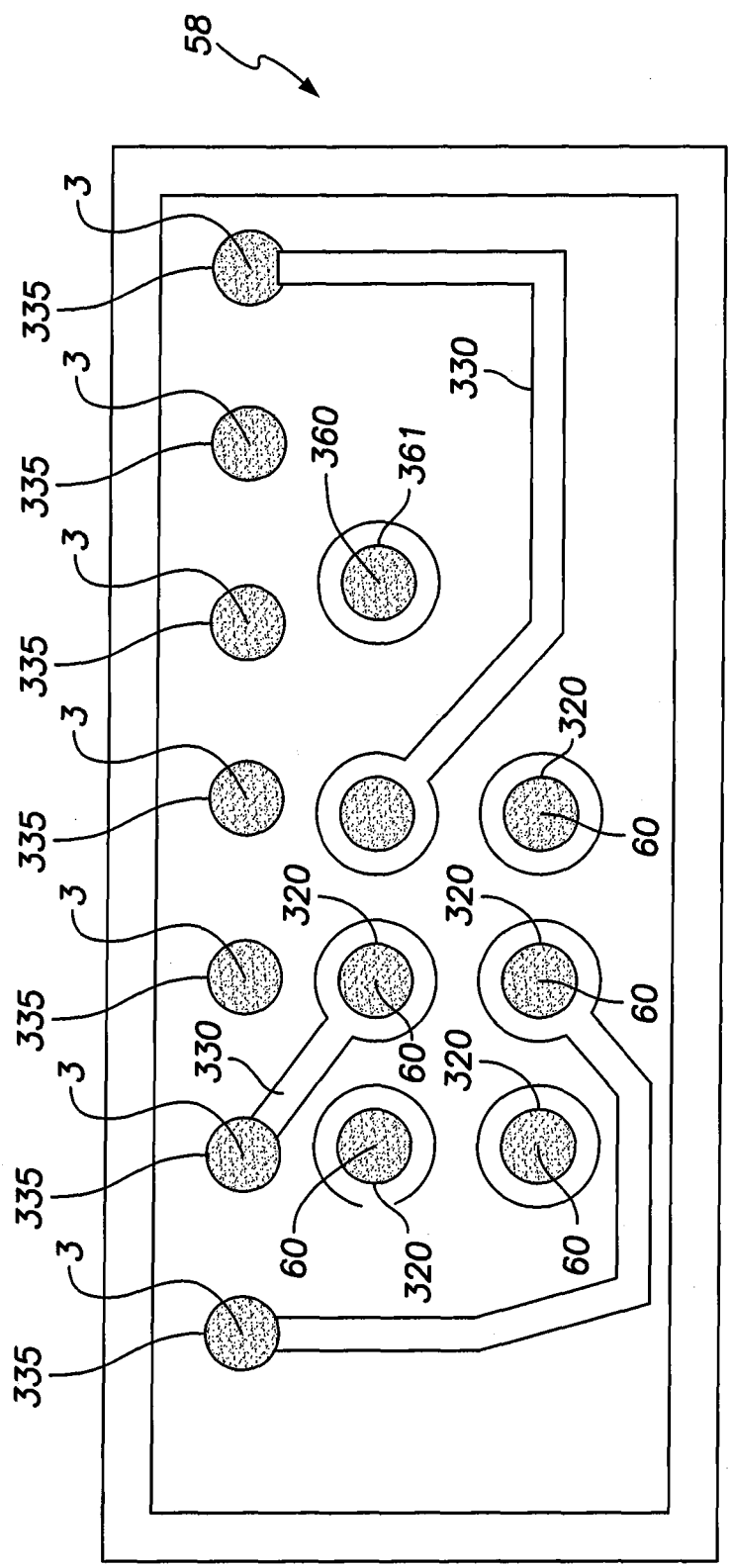

The via holes 320, 335, 361 are used to electrically couple together each respective feedthru wire 60 and the ground wire 360 with a respective wire 3 of the linear array 61. For example, as can be understood from FIGS. 17A-17C, which are, respectively, plan view cross sections taken along section lines 17A-17A, 17B-17B and 17C-17C in FIG. 14, a conductor (e.g., traces, wires, etc.) 330 extends through the body of the board 58 from each respective via hole 320, 361 (and, as a result, the feedthru wire 60 or ground wire 360 contained therein) to another respective via hole 335 containing a respective wire 3 of the linear array 61. Thus, each feedthru wire 60 (and the ground wire 360) is coupled to a respective linear array wire 3 via a dedicated conductor 330 imbedded in, and extending through, the body of the board 58. The conductors 330 are formed of gold, nickel, platinum, etc. and are provided via electroplating, photo deposition, vapor deposition, etc. The material of the body of the board 58 in which the conductors 330 are imbedded is formed of an electrically insulating material such as, for example, ceramic, printed circuit board (PCB), or etc. The conductors 330 are separated from each other by being imbedded in the body of the board 58 in a spaced-apart fashion, as can be understood from FIG. 14 and FIGS. 17A-17C.

The integrated feedthru assembly 55 disclosed herein advantageously provides a configuration that offers reduced size and materials costs. The feedthru assembly 55 also provides improved ease of manufacturing via simply plugging the wires of the feedthru into the board and those of the board into a plug-in type connector electrically coupled to the electronic substrate housed within the can. These benefits facilitate a more compact pulse generator and decreased manufacturing costs.

The above-mentioned benefits are, at least in part, made possible via the feedthru assembly 55 having a grouped or bunched array 59 of feedthru leads 60 that convert to an inline array 61 of leads 3 that are in an inline "connector capable" arrangement. Such a feedthru assembly that can be simply plugged into a connector 2 offers improved manufacturability and reworkability, is easier to transfer to manufacturing sites, and does not require wirebonding equipment, tooling, maintenance, and extensive training, as compared to other feedthru designs.

Figure 19:
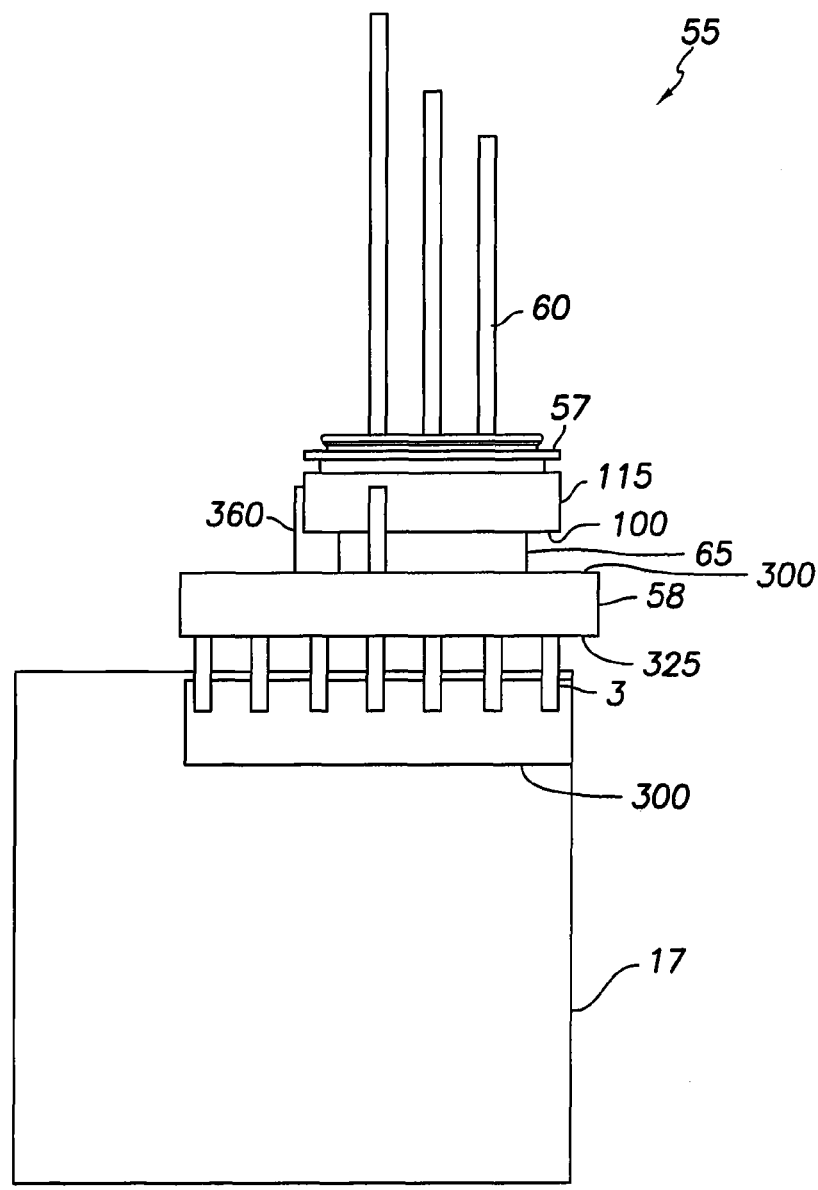
FIG. 19 is a diagrammatic depiction of the linear array wires being electrically coupled to an electrical connection region of an electronic substrate.
Figure 20:
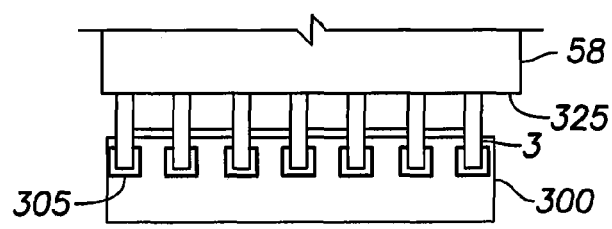
FIG. 20 shows the electrical connection region of the electronic substrate wherein the electrical connection region has wire bond pads or Kovar tabs individually electrically connected to each wire of the linear array wires.

While the preceding discussion is given in the context of the electronic substrate 17 having a plug-in type connector 2 that receives the linear array wires 3 in a plug-in fashion, in other embodiments, the electronic substrate is coupled to the linear array wires 3 via other arrangements. For example, as shown in FIG. 19, the electronic substrate 17 may have an electrical connection region 300 that provides a configuration that enables the linear array wires 3 to be electrically connected to the electronic substrate 17 via wire bonding, welding, soldering or other methods. Such an electrical connection region 300 may include the above discussed plug-in type connector 2 or it may employ other arrangements for achieving an electrical connection with the linear array wires 3. For example, in one embodiment as shown in FIG. 20, the electrical connection region 300 may include wire bonding pads or Kovar tabs 305 with each linear array wire 3 electrically coupled to a respective wire bonding pad or Kovar tab. In yet another embodiment, the electrical connection region 300 may include a portion of the electronic substrate 17 configured for at least one of welding or soldering each wire 3 directly to the electronic substrate without the use of plug-in connectors, bonding pads, or Kovar tabs, the substrate itself being configured to so connect to the wires 3.

Although the present invention has been described with reference to preferred embodiments, persons skilled in the art will recognize that changes may be made in form and detail without departing from the spirit and scope of the invention.

What is claimed is:

1. An implantable pulse generator comprising:
   a header including lead connector blocks;
   a can coupled to the header and including a wall and an electronic substrate housed within the wall, the electronic substrate including an electrical connection region;
   a grouped array feedthru mounted in the wall and comprising:
      a feedthru housing having a header side and a can side;
      an electrically insulative core disposed within the feedthru housing; and
      a grouped array of feedthru wires extending through the electrically insulative core, each feedthru wire having a first end and a second end opposite the first end, the first end electrically coupled to a lead connector block of the lead connector blocks; and
   an inline array feedthru board adjacent the can side and comprising:
      a grouped array of first electrical contact holes receiving therein the second ends; and
   an inline array of conductor wires projecting from a side of the board opposite the feedthru, each first electrical contact hole in electrical communication with a respective conductor wire, and each conductor wire in electrical contact with at least a portion of the electrical connection region.

2. The pulse generator of claim 1, wherein the grouped array of feedthru wires is two rows of four feedthru wires and the inline array of conductor wires is a single line of at least eight conductor wires.

3. The pulse generator of claim 1, wherein the grouped array of feedthru wires is two rows of three feedthru wires and the inline array of conductor wires is a single line of at least six conductor wires.

4. The pulse generator of claim 1, wherein the grouped array of feedthru wires is two rows of two feedthru wires and the inline array of conductor wires is a single line of at least four conductor wires.

5. The pulse generator of claim 1, further comprising an EMI filter coupled to the feedthru.

6. The pulse generator of claim 5, wherein the EMI filter is sandwiched between the feedthru and board, and the grouped array of feedthru wires extend through the EMI filter before being received in the grouped array of first electrical contact holes.

7. The pulse generator of claim 5, wherein the EMI filter includes at least one of a discoidal capacitor or a discrete capacitor.

8. The pulse generator of claim 1, wherein the board includes respective conductive traces extending through a body of the board so each first electrical contact hole is in electrical communication with a respective conductor wire.

9. The pulse generator of claim 7, further comprising a ground wire extending from the board on a side opposite a side from which the conductor wires extend, the ground wire being in electrical contact with a conductor wire of the inline array and a housing of the feedthru.

10. The pulse generator of claim 1, wherein the electrical connection region includes a plug-in type electrical connector having an inline array of second electrical contact holes and each conductor wire is received in a respective second electrical contact hole.

11. The pulse generator of claim 1, wherein the electrical connection region includes at least one of wire bonding pads or Kovar tabs and each conductor wire is electrically coupled to a respective pad or tab.

12. The pulse generator of claim 1, wherein the electrical connection region includes a portion of the electronic substrate configured for at least one of wire bonding, welding or soldering each conductor wire to the portion of the electronic substrate.

13. An implantable pulse generator comprising:
a header including lead connector blocks;
a can coupled to the header and including a wall and an electronic substrate housed within the wall, the electronic substrate including an electrical connection region; and
a feedthru assembly including a feedthru mounted in the wall and a feedthru board coupled to the feedthru and housed within the wall, the feedthru having a feedthru housing and an electrically insulative core disposed within the feedthru housing;
wherein a grouped array of feedthru wires extends from the connector blocks, through the electrically insulative core and into the feedthru board;
wherein a linear array of conductor wires extends from a side of the board opposite the feedthru;
wherein each feedthru wire is in electrical communication with a respective conductor wire; and
wherein each conductor wire is received in the electrical connection region.

14. The pulse generator of claim 13, wherein the grouped array of feedthru wires is two rows of four feedthru wires and the linear array of conductor wires is a single line of at least eight conductor wires.

15. The pulse generator of claim 13, wherein the grouped array of feedthru wires is two rows of three feedthru wires and the linear array of conductor wires is a single line of at least six conductor wires.

16. The pulse generator of claim 13, wherein the grouped array of feedthru wires is two rows of two feedthru wires and the linear array of conductor wires is a single line of at least four conductor wires.

17. The pulse generator of claim 13, further comprising an EMI filter coupled to the feedthru.

18. The pulse generator of claim 17, wherein the EMI filter is sandwiched between the feedthru and board, and the grouped array of feedthru wires extend through the EMI filter before extending into the board.

19. The pulse generator of claim 17, wherein the EMI filter includes at least one of a discoidal capacitor or a discrete capacitor.

20. The pulse generator of claim 13, wherein the board includes respective conductive traces extending through a body of the board so each feedthru wire is in electrical communication with a respective conductor wire.

21. The pulse generator of claim 20, further comprising a ground wire extending from the board on a side opposite a side from which the conductor wires extend, the ground wire being in electrical contact with a conductor wire of the linear array and a housing of the feedthru.

22. The pulse generator of claim 13, wherein the electrical connection region includes a plug-in type electrical connector having a linear array of electrical contact holes and each conductor wire is received in a respective electrical contact hole.

23. The pulse generator of claim 13, wherein the electrical connection region includes at least one of wire bonding pads or Kovar tabs and each conductor wire is electrically coupled to a respective pad or tab.

24. The pulse generator of claim 13, wherein the electrical connection region includes a portion of the electronic substrate configured for at least one of wire bonding, welding or soldering each conductor wire to the portion of the electronic substrate.

25. A method of manufacturing an implantable pulse generator, the method comprising:
providing a feedthru assembly having a feedthru with a feedthru housing, an electrically insulative core disposed within the feedthru housing, and a bunched array of feedthru wires extending from a header side of the feedthru and a linear array of conductor wires extending from a can side of a feedthru board of the assembly, the feedthru board being adjacent a can side of the feedthru;
coupling the bunched array of feedthru wires to connector blocks in a header of the pulse generator; and
extending the linear array of conductor wires into an electrical connection region of an electronic substrate housed within a can of the pulse generator.

26. The method of claim 25, wherein extending the linear array of conductor wires into an electrical connection region includes plugging the linear array of conductor wires into a linear array of contact holes of a plug-in type connector electrically coupled to the electronic substrate housed within the can of the pulse generator.

27. The method of claim 25, wherein the feedthru assembly is configured to transition the bunched array of feedthru wires into the linear array of conductor wires.

28. The method of claim 27, wherein the feedthru assembly includes an EMI filter sandwiched between the feedthru and feedthru board, and the bunched array of feedthru wires extends through the EMI filter and into the feedthru board.

29. The method of claim 25, wherein the bunched array of feedthru wires includes multiple rows of multiple feedthru wires, and the linear array of conductor wires includes a singe line of multiple conductor wires.

30. The method of claim 25, wherein extending the linear array of conductor wires into an electrical connection region includes electrically coupling the linear array of conductor wires to at least one of wire bond pads or Kovar tabs electrically coupled to the electronic substrate housed within the can of the pulse generator.

* * * * *